(12) United States Patent
Estes et al.

(10) Patent No.: US 12,379,264 B2
(45) Date of Patent: Aug. 5, 2025

(54) SELF-CALIBRATING TEMPERATURE SENSING APPARATUS FOR USE WITH A PHOTO-THERMAL TARGETED TREATMENT SYSTEM AND ASSOCIATED METHODS

(71) Applicant: Accure Acne, Inc., Boulder, CO (US)

(72) Inventors: Michael John Estes, Lafayette, CO (US); Henrik Hofvander, Budapest (HU); Aubrey Jean Eck, Arvada, CO (US)

(73) Assignee: Accure Acne, Inc., Boulder, CO (US)

( * ) Notice: Subject to any disclaimer, the term of this patent is extended or adjusted under 35 U.S.C. 154(b) by 65 days.

(21) Appl. No.: 18/244,589

(22) Filed: Sep. 11, 2023

(65) Prior Publication Data
US 2023/0417608 A1 Dec. 28, 2023

Related U.S. Application Data

(63) Continuation-in-part of application No. 17/867,210, filed on Jul. 18, 2022, now Pat. No. 11,754,450,
(Continued)

(51) Int. Cl.
*G01K 15/00* (2006.01)
*A61B 3/00* (2006.01)
(Continued)

(52) U.S. Cl.
CPC ............ *G01K 15/005* (2013.01); *A61N 5/00* (2013.01); *A61N 5/06* (2013.01); *A61N 5/0616* (2013.01);
(Continued)

(58) Field of Classification Search
CPC ........ G01K 15/005; G01K 1/143; G01K 7/02; A61N 5/00; A61N 5/06; A61N 5/0616;
(Continued)

(56) References Cited

U.S. PATENT DOCUMENTS

| 2004/0254472 | A1 | 12/2004 | Mcquilkin |
| 2007/0138394 | A1* | 6/2007 | Lane ........................ G01J 5/02 250/353 |

OTHER PUBLICATIONS

Canadian Intellectual Property Office, "Office Action in Canadian Patent Application No. 3,127,861", mailing date Jul. 11, 2023, 4 pages.

* cited by examiner

*Primary Examiner* — Wei (Victor) Y Chan
(74) *Attorney, Agent, or Firm* — Kilpatrick Townsend & Stockton LLP

(57) ABSTRACT

A scanner arrangement for a temperature measurement system for measuring a temperature of a measured surface is disclosed. The scanner arrangement includes a first temperature sensor and a reference assembly. The reference assembly includes an opening including a reference surface, a second temperature sensor in contact with and for measuring the temperature of the reference surface, and a heater for heating the reference surface in accordance with control signals from a controller. The first temperature sensor has a field of view covering a portion of the measured surface and the reference surface. In embodiments, the temperature measurement system is integrated into a photo-thermal treatment unit providing a cooling air stream and laser energy, controlled by the controller. The opening and reference surface cooperate such that the reference surface is protected from direct exposure to the cooling air stream and the laser energy.

9 Claims, 16 Drawing Sheets

Related U.S. Application Data which is a continuation of application No. 16/734,280, filed on Jan. 3, 2020, now Pat. No. 11,391,634.

(60) Provisional application No. 62/804,719, filed on Feb. 12, 2019.

(51) Int. Cl.
| | |
|---|---|
| *A61B 90/00* | (2016.01) |
| *A61N 5/00* | (2006.01) |
| *A61N 5/06* | (2006.01) |
| *G01J 5/00* | (2022.01) |
| *G01K 1/143* | (2021.01) |
| *G01K 7/02* | (2021.01) |
| *G01K 7/22* | (2006.01) |

(52) U.S. Cl.
CPC .............. *G01J 5/00* (2013.01); *G01K 1/143* (2013.01); *A61B 3/0008* (2013.01); *A61B 90/361* (2016.02); *A61B 2562/0271* (2013.01); *A61B 2562/14* (2013.01); *G01K 7/02* (2013.01); *G01K 7/22* (2013.01)

(58) Field of Classification Search
CPC ........ G01J 5/00; A61B 90/361; A61B 3/0008; A61B 2562/0271; A61B 2562/14
See application file for complete search history.

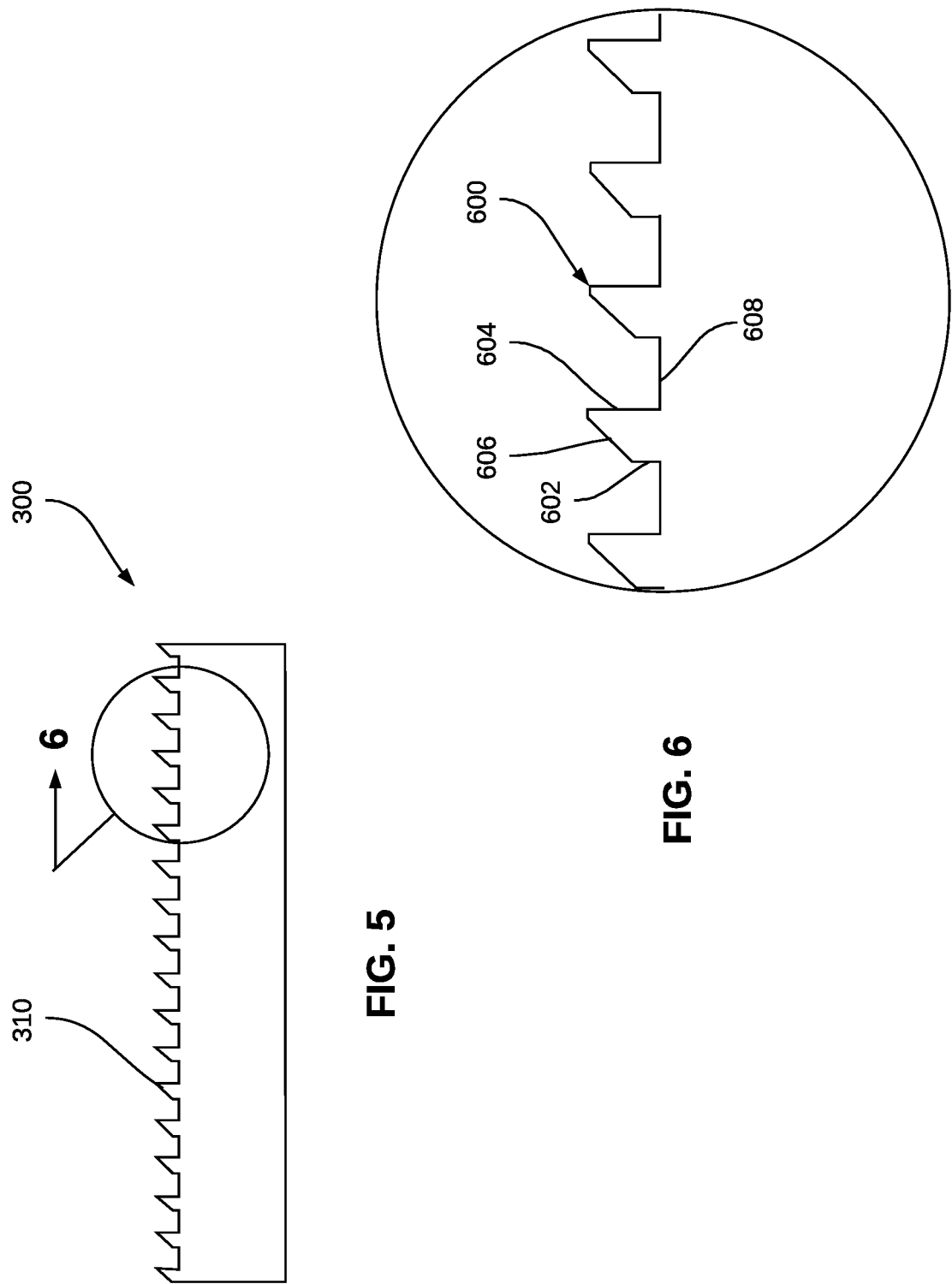

SELF-CALIBRATING TEMPERATURE SENSING APPARATUS FOR USE WITH A PHOTO-THERMAL TARGETED TREATMENT SYSTEM AND ASSOCIATED METHODS

REFERENCE TO RELATED APPLICATIONS

The present application is a continuation-in-part of copending U.S. patent application Ser. No. 17/867,210, filed 2022 Jul. 18 and titled "Temperature Sensing Apparatus for Use with a Photo-Thermal Targeted Treatment System and Associated Methods," which in turn is a continuation of U.S. patent application Ser. No. 16/734,280, now U.S. Pat. No. 11,391,634, filed 2020 Jan. 3 and titled "Temperature-Sensing Apparatus for Use with a Photo-Thermal Targeted Treatment System and Associated Methods," which claims the benefit of U.S. Provisional Patent Application Ser. No. 62/804,719, filed 2019 Feb. 12 and titled "Temperature-Sensing Apparatus for Use with a Photo-Thermal Targeted Treatment System and Associated Methods." All of the above referenced applications are incorporated hereby in their entirety by reference.

FIELD OF THE INVENTION

The present invention relates to energy-based treatments and, more specifically, systems and methods for improving the accuracy of temperature measurements used during an energy-based dermatological treatment.

DESCRIPTION OF RELATED ART

Sebaceous glands and other chromophores embedded in a medium such as the dermis, can be thermally damaged by heating the chromophore with a targeted light source, such as a laser. However, the application of enough thermal energy to damage the chromophore can also be damaging to the surrounding dermis and the overlying epidermis, thus leading to epidermis and dermis injury as well as pain to the patient.

Previous approaches to prevent epidermis and dermis injury, as well as patient pain include:
1. Cooling the epidermis, then applying the photo-thermal treatment; and
2. Cool the epidermis, also condition (i.e., preheat) the epidermis and dermis in a preheating protocol, then apply photo-thermal treatment in a separate treatment protocol. In certain instances, the preheating protocol and the treatment protocol are performed by the same laser, although the two protocols involve different laser settings and application protocols, thus leading to further complexity in the treatment protocol and equipment.

For either of these approaches, as well as in many energy-based dermatological procedures, measuring the temperature of the skin surface during the treatment provides valuable information that can be used to adjust the treatment protocol and/or equipment settings in real time. For example, there are contact-less temperature measurement methods, such as those based on optical and imaging techniques, that provide useful avenues for measuring skin surface temperatures during dermatological procedures.

However, accurate contact-less measurements of the skin surface are challenging to perform, particularly when the dermatological procedure involves external mechanisms that can affect the temperature measurement apparatus as well as the skin temperature. For instance, the use of air cooling prior to and during the dermatological procedure can cool the skin surface as well as impact the performance of the sensor that is making the contact-less skin surface measurement.

As an example, one approach to make contact-less skin surface temperature measurements is to utilize a multi-pixel infrared (IR) sensor, such as an IR camera. For IR cameras, the measurement uniformity (i.e., the difference in temperature measured by different pixels of the IR camera when viewing a surface with a uniform temperature) is quite good. However, the absolute accuracy (i.e., the absolute recorded value of the temperature measured by each pixel or by averaging the measurements recorded by several adjacent pixels) has a measurement error that may prohibit the use of a contact-less sensor for skin surface measurements. For instance, even the most sophisticated IR cameras are subject to poor absolute accuracy, where a surface measured as 5° C. is actually at 8° C. due to a calibration offset error in the camera.

Another inaccuracy phenomenon is "camera drift" where the accuracy of the camera varies over time, such as due to changes in the overall environmental temperature of the environment in which the procedure is taking place, or for reasons related to the dermatological procedure, such as when, over time, a laser source heats the structure onto which the camera is mounted or when spill-over air from air cooling impinges on the camera and affects the temperature of the camera body, which in turn leads to a measurement error.

SUMMARY OF THE INVENTION

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

In accordance with the embodiments described herein, there is disclosed a temperature measurement system for measuring a temperature of a measured surface. The system includes: 1) a first temperature sensor; and 2) a reference surface including a second temperature sensor integrated therein. The first temperature sensor includes a field of view simultaneously covering both at least a portion of the measured surface and at least a portion of the reference surface, thus is configured for simultaneously taking a first measurement of both the portion of the measured surface and the portion of the reference surface.

The first measurement of the reference surface taken by the first temperature sensor is compared to a second measurement taken by the second temperature sensor for use in calibrating the first temperature sensor. In an example, the second temperature sensor includes one or more individual sensors in the cases where redundancy is desired, for instance. The first measurement is then adjusted using the reading made by the second temperature sensor.

In accordance with another embodiment, a photo-thermal targeted treatment system for targeting a chromophore embedded in a medium includes a controller; a photo-thermal treatment unit; and a temperature measurement system for measuring a temperature of a measured surface covering at least a portion of the medium. The controller is configured for administering a treatment protocol using the photo-thermal treatment unit. The temperature measurement system includes 1) a first temperature sensor, and 2) a reference surface with a second temperature sensor integrated therein, wherein the first temperature sensor includes a field of view simultaneously covering both at least a portion of the measured surface and at least a portion of the reference surface.

In accordance with yet another embodiment, a method for continuously calibrating a temperature measurement system for use with a dermatological treatment includes: 1) using a first temperature sensor, simultaneously taking a first measurement of a measured surface and a first reference measurement of a reference surface; 2) using a second temperature sensor embedded within a reference surface, taking a second reference measurement of the reference surface; 3) calculating a comparison value between the first and second reference measurements; and 4) calibrating the first temperature sensor in accordance with the comparison value.

In accordance with an embodiment, a scanner arrangement for a temperature measurement system for measuring a temperature of a measured surface includes a first temperature sensor and a reference assembly. The reference assembly includes an opening with a reference surface located within the opening, a second temperature sensor positioned in contact with the reference surface and configured for measuring temperature of the reference surface, and a heater for heating the reference surface in accordance with control signals from a controller. The first temperature sensor is a contactless temperature sensor with a field of view covering at least a portion of the measured surface and at least a portion of the reference surface.

In embodiments, the temperature measurement system is integrated into a photo-thermal treatment unit configured for providing a cooling air stream and laser energy toward the measured surface. In embodiments, the controller also controls the cooling air stream and the laser energy, and the opening and the reference surface are configured to cooperate such that the reference surface is protected from direct exposure to the cooling air stream and the laser energy.

In embodiments, the reference surface is set back from a mouth of the opening.

In embodiments, the scanner arrangement further includes a baffle for directing stray portions of the cooling air stream and the laser energy away from the reference surface.

In embodiments, the first temperature sensor is an infrared camera. The second temperature sensor may be a contact sensor. In certain embodiments, the contact sensor includes at least one of an integrated circuit temperature measurement device, a resistive temperature detector, a thermocouple, and a thermistor. The second temperature sensor may also include two or more contact sensors.

In embodiments, the heater is configured for heating the reference surface to an elevated temperature within 0-20° C. of a measured temperature of the measured surface.

In embodiments, the reference surface is characterized by a reference emissivity value approximately equal to a measured emissivity value of the measured surface.

In another embodiment, a photo-thermal targeted treatment system for targeting a chromophore embedded in a medium includes a controller, a photo-thermal treatment unit, and a temperature measurement system for measuring a temperature of a measured surface covering at least a portion of the medium. The controller may be configured for administering a treatment protocol using the photo-thermal treatment unit.

In embodiments, the photo-thermal treatment unit is configured for providing a cooling air stream and laser energy toward the measured surface. In embodiments, the temperature measurement system includes 1) a first temperature sensor and 2) a reference assembly. The reference assembly may include an opening with a reference surface located within the opening, a second temperature sensor positioned in contact with the reference surface and configured for measuring temperature of the reference surface, and a heater for heating the reference surface in accordance with control signals from the controller. The first temperature sensor may be a contactless temperature sensor with a field of view covering at least a portion of the measured surface and at least a portion of the reference surface. The opening and the reference surface are configured to cooperate such that the reference surface is protected from direct exposure to the cooling air stream and the laser energy.

In certain embodiments, a first measurement taken by the first temperature sensor is compared to a second measurement taken by the second temperature sensor for use in calibrating the first temperature measurement with respect to the second temperature measurement.

In embodiments, the first and second measurements are taken in situ during the treatment protocol. In embodiments, the first and second measurements are used by the controller to modify the treatment protocol in progress. In embodiments, the first and second measurements are used by the controller to terminate or initiate the treatment protocol in accordance therewith.

In certain embodiments, a time response of the measured surface temperature is used to estimate an underlying dermis temperature, thereby providing a more accurate estimate of the chromophore targeted by the photo-thermal targeted treatment system than would be possible without the temperature measurement system.

In certain embodiments, the opening and the reference surface are configured to cooperate such that the reference surface is protected from direct exposure to the cooling air stream and the laser energy. In embodiments, the reference surface is set back from a mouth of the opening. In embodiments, the system further includes a baffle for directing stray portions of the cooling air stream and the laser energy away from the reference surface. In embodiments, the reference surface may be disposed closer to the mouth of the opening in the reference assembly, relying solely on the baffle to deflect stray cooling air stream and laser energy away from the reference surface.

In another embodiment, a method for operating a self-calibrating temperature sensing apparatus is disclosed. The method includes activating a first temperature sensor, and activating a reference assembly. The reference assembly may include an opening with a reference surface located within the opening, a second temperature sensor positioned in contact with the reference surface and configured for measuring temperature of the reference surface, and a heater for heating the reference surface. The method further includes measuring a contactless temperature reading of a target surface and the reference surface with the first temperature sensor, and measuring a contact temperature reading of the reference surface using the second temperature sensor. The method may further include comparing the contactless temperature reading and the contact temperature reading of the reference surface, and calibrating the contactless temperature reading of the target surface to calculate a calibrated target surface temperature.

In embodiments, the method further includes integrating the calibrated target surface temperature with a thermal gradient model. In embodiments, the method further includes estimating a starting temperature of the target surface, and heating the reference to the starting temperature using the heater.

In embodiments, the method further includes heating the reference surface to an elevated temperature within 0-20° C. of the contactless temperature reading of the target surface.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF DRAWINGS

FIG. 5 is a side view of the reference surface, in accordance with an embodiment.

FIG. 6 is an enlarged view of an inset of the reference surface of FIG. 5.

Figure 1:
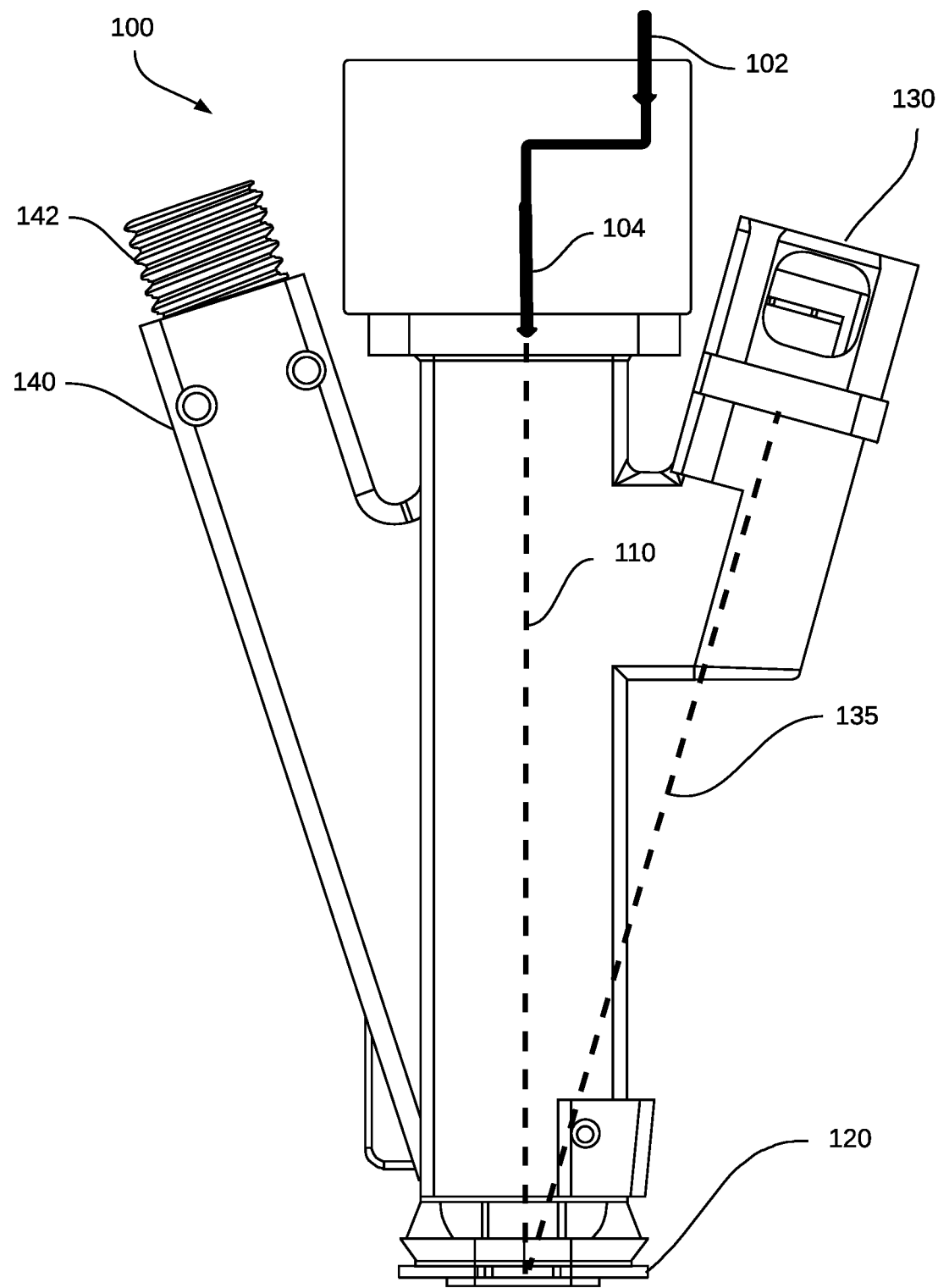
FIG. 1 illustrates a partial cutaway view of a portion of a scanner apparatus suitable for use with a photo-thermal treatment system, in accordance with an embodiment

For simplicity and clarity of illustration, the drawing figures illustrate the general manner of construction, and descriptions and details of well-known features and techniques may be omitted to avoid unnecessarily obscuring the embodiments detailed herein. Additionally, elements in the drawing figures are not necessarily drawn to scale. For example, the dimensions of some of the elements in the figures may be exaggerated relative to other elements to help improve understanding of the described embodiments. The same reference numerals in different figures denote the same elements.

The word "exemplary" is used herein to mean "serving as an example, instance, or illustration." Any embodiment described herein as "exemplary" is not necessarily to be construed as preferred or advantageous over other embodiments. In the following detailed description, references are made to the accompanying drawings that form a part hereof, and in which are shown by way of illustrations or specific examples. These aspects may be combined, other aspects may be utilized, and structural changes may be made without departing from the present disclosure. Example aspects may be practiced as methods, systems, or apparatuses. The following detailed description is therefore not to be taken in a limiting sense, and the scope of the present disclosure is defined by the appended claims and their equivalents.

DETAILED DESCRIPTION OF THE INVENTION

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity. Like numbers refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "under," "above," "upper," and the like, may be used herein for ease of description to describe one element or feature's relationship to another element(s) or feature(s)

as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/".

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present. Likewise, when light is received or provided "from" one element, it can be received or provided directly from that element or from an intervening element. On the other hand, when light is received or provided "directly from" one element, there are no intervening elements present.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

In laser treatment of acne, the operating thermal range is generally bound on the upper end at the epidermis and dermis damage threshold temperature of approximately 55° C., and at the lower end by the temperature required to bring the sebaceous gland to its damage threshold temperature of approximately 55° C. Based on clinical data, the operating temperature range for acne treatment expressed in terminal skin surface temperature is approx. to 55° C., as an example. At skin surface temperatures below 45° C., it has been determined that there is little to no damage to the sebaceous gland. When the skin surface temperature is between 45° C. and 55° C., there are varying degrees of sebaceous gland damage, with no epidermal damage. Above 55° C., there is epidermal damage in addition to damage to the sebaceous gland. In embodiments, a safer operating temperature range may be in the range of to 50° C. at the skin surface, as there is virtually no damage to the target sebaceous gland, below 40° C., while damage to the epidermis becomes more likely above 50° C.

While there is not a good way to directly measure the temperature of the sebaceous gland being targeted by the treatment protocol, the skin surface temperature can be an indicator of the sebaceous gland temperature. A correlation model providing the correspondence between sebaceous gland temperature and skin surface temperature can then be used to tailor the actual treatment protocol using skin surface temperature measurements for effectively targeting sebaceous gland damage while staying below the damage threshold for the epidermis and dermis. The correlation model can be developed using, for example, an analytical heat transfer model, or by using clinical data (e.g., via biopsies) correlating skin surface temperature to sebaceous gland damage given the application of a specific treatment protocol.

However, while such correlation models can be incorporated into the treatment protocols, the effectiveness and safety of the treatment are still predicated on the accuracy of the skin surface temperature measurement. As mentioned above, there are various contactless methods of measuring skin surface temperature during, for example, dermatological procedures. Devices such as infrared (IR) cameras, pyrometers, bolometers, and dual-wavelength sensors can provide a reading of the skin surface temperature. However, for procedures such as photo-thermal targeted treatment to cause thermal damage to subcutaneous sebaceous glands, accurate, calibrated reading of the skin surface temperature can prevent damage to the epidermis and dermis in and around the treatment area.

The system and associated methods described herein provides a fast, inexpensive, and compact system and method to significantly improve the accuracy of contactless temperature measurements. While much of the discussion below refers to the use of an IR camera as the temperature sensor, any suitable contactless temperature measurement device can be substituted for the IR camera and fall within the scope of the present disclosure.

Turning now to the figures, FIG. 1 illustrates a side view of a portion of a scanner apparatus suitable for use with a photo-thermal treatment system, in accordance with an embodiment. A scanner 100 includes an optical fiber 102 for transmitting a laser beam 104 from a base station (not shown) along an laser beam path 110 toward a treatment tip 120, which is placed in contact with the treatment location. Scanner 100 can optionally include optical components for shaping the light beam projected onto the skin at treatment tip 120. Treatment tip 120 serves as a visual guide for the user to position scanner 100 at a desired treatment location. In order to allow contactless temperature measurement, an IR camera 130 is attached to scanner 100 and pointing downward toward treatment tip 120 such that IR camera 130 is able to detect the temperature of the treatment location along an optical path 135. In an embodiment, IR camera 130 has a fast time response of less than 40 milliseconds between consecutive surface temperature measurements. Additionally, in the embodiment shown in FIG. 1, scanner 100 includes a cooling air duct 140. As an example, an air hose (not shown) can be attached to cooling air duct 140 via a threaded opening 142.

Figure 2:
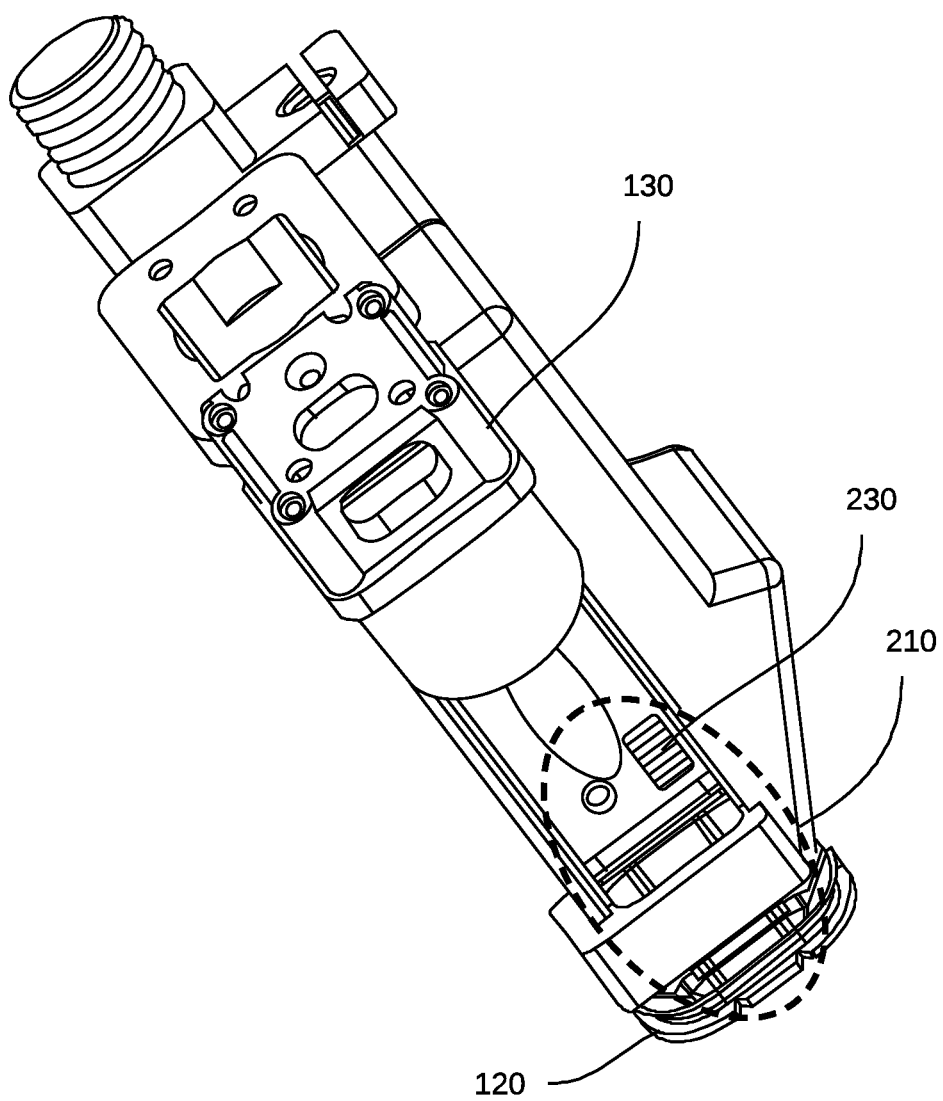
FIG. 2 is a diagram illustrating a field of view (FoV) of a thermal sensor, in accordance with an embodiment.

FIG. 2 illustrates a field of view (FoV) of IR camera 130 looking toward treatment tip 120. FoV 210 (represented by an oval) of the IR camera, in accordance with an embodiment. Visible within FoV 210 are treatment tip 120 and a reference surface 230, attached to an inner surface of scanner 100. Thus, IR camera 130 is capable of simultaneously measuring the temperature of treatment area 222 and reference surface 230.

Figure 3:
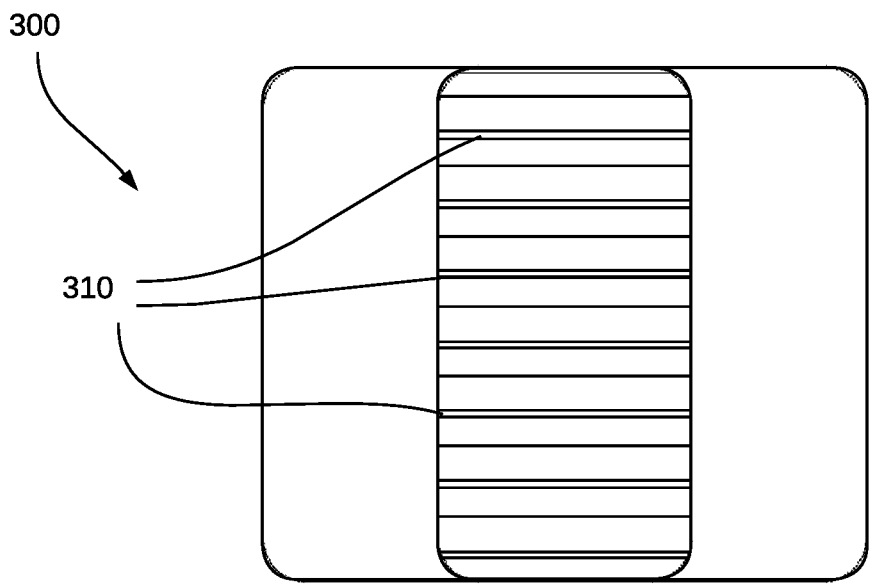
FIG. 3 is a front view of a reference surface for use with a photo-thermal treatment system, in accordance with an embodiment.
Figure 4:
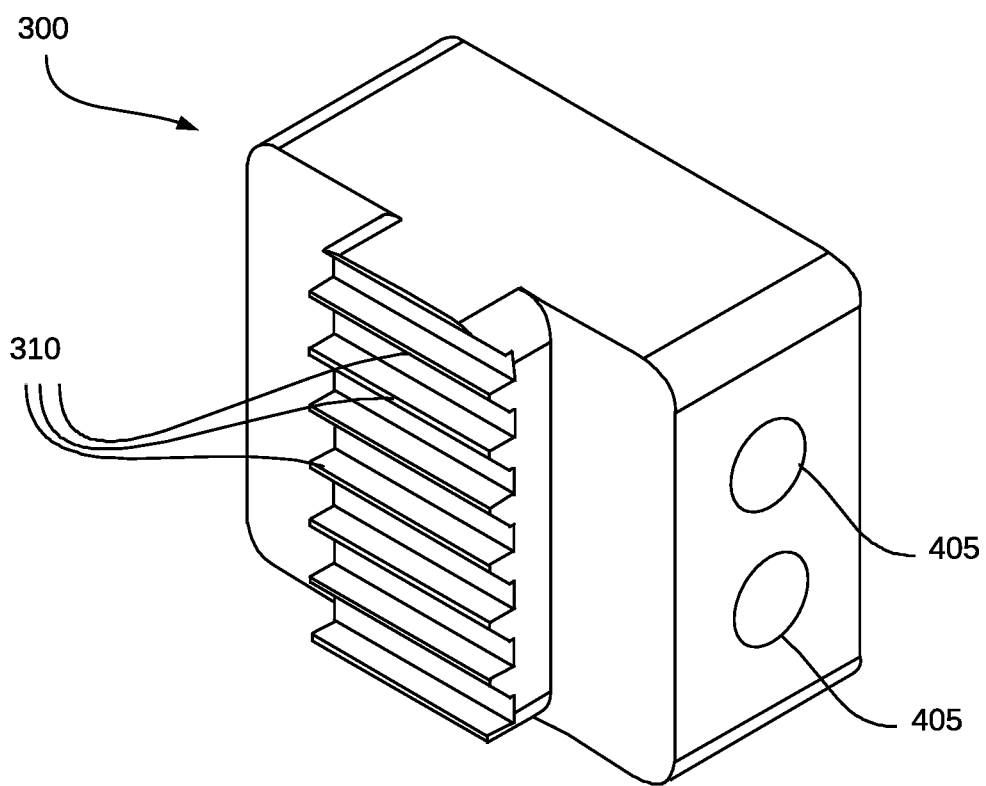
FIG. 4 is an ISO view of the reference surface, as viewed diagonally from the bottom, in accordance with an embodiment.

Further details of the reference surface, in accordance with an embodiment, are illustrated in FIGS. 3-6. FIG. 3 is a front view of a reference surface and FIG. 4 is an ISO view of the reference surface, as viewed diagonally from the bottom, in accordance with an embodiment. As shown in FIGS. 3 and 4, a front surface of reference surface 300 includes a texture 310, which steers reflections and stray light from any surface other, than the reference surface itself, away from FoV 210. In an exemplary embodiment, reference surface 300 also includes one or more mounting holes (not shown) through which reference surface 300 can be attached to, for example, an inside surface of scanner 100 as shown in FIG. 2. Alternatively, reference surface 300 is captively attached or otherwise mounted onto an appropriate location within the FoV of the IR camera. In an embodiment, the reference surface is characterized by a reference emissivity value approximately equal to a measured emissivity value of the measured skin surface. In another example, a surface coating on the reference surface exhibits a light scattering property that is approximately Lambertian, not specular.

Also, as visible in the example illustrated in FIG. 4, reference surface 300 includes one or more insertion holes 405 into which a contact temperature sensor (not shown), such as an integrated circuit temperature measurement device, a resistive temperature detector, a thermocouple, or a thermistor, is placed for directly measuring the temperature of reference surface 300. Alternatively, a contact temperature sensor can be directly attached or otherwise integrated into reference surface 300. The contact temperature sensor can be in direct contact with the reference surface and, in an embodiment, the contact temperature sensor is embedded into the reference surface. Suitable direct contact temperature sensors include thermistors, and should be chosen to provide highly accurate temperature measurements with low noise and low drift. In an embodiment, the contact temperature sensor exhibits high measurement accuracy (e.g., accurate to within 0.1° C.). The contact temperature sensor should have good thermal contact with the reference surface. For example, thermal paste or thermal adhesive is used between the contact temperature sensor and the reference surface such that the temperature measurement by the contact temperature sensor closely corresponds to the temperature of the reference surface. In an embodiment, the reference surface is formed of a material with high thermal conductivity, such as copper or aluminum, such that the reference surface temperature as measured by the IR camera is substantially equal to the internal temperature of the reference surface as measured by the contact temperature sensor.

FIG. 5 is a side view of the reference surface, in accordance with an embodiment. As can be seen in FIG. 5, texture 310 has a sawtooth shape in this exemplary embodiment. If a flat, smooth reference surface is used, reflections from other surfaces may bounce off the reference surface and enter the field of view of the camera, thus potentially causing a temperature measurement error. By including a texturing on a front surface of the reference surface, any reflections from outside surfaces are directed away from the FoV of the IR camera such that the camera only sees the reference surface itself along with the treatment area.

Further details of texture 310 are shown in FIG. 6, which shows an enlarged view of an inset of the reference surface of FIG. 5. As shown in FIG. 6, each sawtooth feature 600 of texture 310 includes a first height 602, a second height 604 and an angled surface 606, and the sawtooth features are separated by a distance 608. First height 602, second height 604, angled surface 606, and distance 608 are configured such that the collective structure serves as a light baffle and/or reflector for directing stray light away from FoV 210. It is noted that other textures are also contemplated, such as textures used in beam traps, light baffles, and laser beam dumps.

As an alternative, the temperature measurement system can also be arranged such that the first temperature sensor periodically measures the temperature of the reference surface in certain time intervals. For example, the reference surface can be included in the field of view of the first temperature sensor as described above, or periodic measurement of the reference surface temperature can be made by the first temperature sensor by scanning the field of view of the temperature sensor using, for example, a scanning mirror located in between the first temperature sensor and the measured surface.

Figure 7:
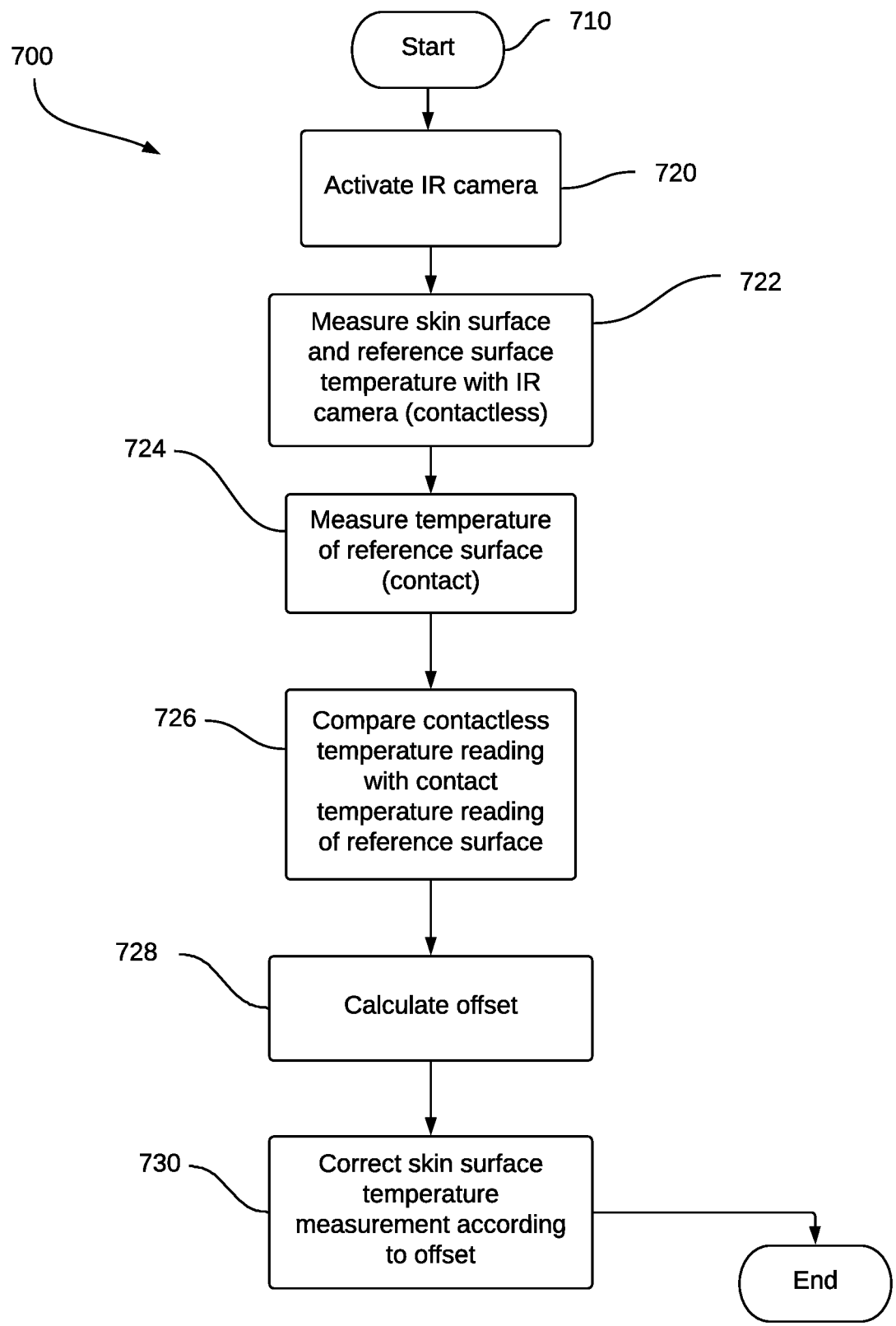
FIG. 7 is a flow diagram illustrating an exemplary contactless method of sensing the temperature of the skin surface, in accordance with an embodiment.

FIG. 7 is a flow diagram illustrating an exemplary contactless method of sensing the temperature of the skin surface, in accordance with an embodiment. As shown in FIG. 7, a process 700 begins with a start step 710, in which the temperature sensing protocol is activated. Then, in a step 720, an IR camera in a setup such as shown in FIG. 1 is activated. IR camera then measures the skin surface temperature and the reference surface temperature in a step 722. It is noted that some IR cameras have an internal self-correction/calibration/shutter mechanism. One such self-correction is a so-called "flat field correction," which ensures that each pixel in the camera measures the same temperature of a constant-temperature surface. The method described in FIG. 7 uses a reference surface that is provided externally to the IR camera. In parallel, a temperature reading of the reference surface is taken with the contact sensor within the reference surface in a step 724. In a step 726, the reference surface temperature taken by the IR camera in step 722 is compared with the temperature reading of the reference surface taken with the contact sensor within the reference surface in step 724. An offset, if any, between the temperature measured in step 722 and the reading taken in step 724 is calculated in a step 728. In a step 730, the offset calculated in 728 is used to correct the skin surface temperature measurement taken by the IR camera. Process 700 is ended in an end step 740.

In other words, by comparing the reference surface temperature, as measured by the contact-less sensor, with a known, high accuracy contact measurement taken of the same reference surface, an offset is calculated, which is used to correct the temperature reading of the skin surface. As a result, the accuracy of the contact-less measurement is greatly improved, regardless of the specific treatment protocol, skin cooling procedures, patient parameters (e.g., age, gender, ethnicity, specific treatment location). It is noted that the contact temperature measurement taken in step 724 of process 700 does not need to occur with every contactless temperature measurement taken in 722. For example, after the offset has been calculated once, steps 724, 726, 728, and 730 can be performed periodically to correct for potential calibration errors.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention.

Accordingly, many different embodiments stem from the above description and the drawings. It will be understood that it would be unduly repetitious and obfuscating to literally describe and illustrate every combination and subcombination of these embodiments. As such, the present specification, including the drawings, shall be construed to constitute a complete written description of all combinations and subcombinations of the embodiments described herein, and of the manner and process of making and using them, and shall support claims to any such combination or subcombination.

For example, embodiments such as the below are contemplated:

1. A scanner arrangement for a temperature measurement system for measuring a temperature of a measured surface, the scanner arrangement including: 1) a first temperature sensor; and 2) a reference surface including a second temperature sensor integrated therein. The first temperature sensor includes a field of view simultaneously covering both at least a portion of the measured surface and at least a portion of the reference surface, thus is configured for simultaneously taking a first measurement of both the portion of the measured surface and the portion of the reference surface. The first measurement of the reference surface taken by the first temperature sensor is compared to a second measurement taken by the second temperature sensor for use in calibrating the first temperature sensor.
2. The scanner arrangement of Item 1, wherein the first temperature sensor is an infrared camera.
3. The scanner arrangement of Item 1, wherein the second temperature sensor is a contact sensor.
4. The scanner arrangement of Item 3, wherein the contact sensor includes at least one of an integrated circuit temperature measurement device, a resistive temperature detector, a thermocouple, and a thermistor.
5. The scanner arrangement of Item 1, wherein the reference surface includes a texture thereon.
6. The scanner arrangement of Item 5, wherein the texture is configured for directing any outside surface, other than from the reference surface, away from the field of view of the first temperature sensor.
7. The scanner arrangement of Item 6, wherein the texture includes a sawtooth pattern.
8. The scanner arrangement of Item 1, wherein the reference surface is characterized by a reference emissivity value approximately equal to a measured emissivity value of the measured surface.
9. The scanner arrangement of Item 8, wherein the reference surface is formed of a material characterized by the reference emissivity value.
10. The scanner arrangement of Item 8, wherein the reference surface is coated with a material characterized by the reference emissivity value.
11. The scanner arrangement of Item 1, wherein the reference surface includes a temperature stabilization mechanism.
12. The scanner arrangement of Item 1, further including a second reference surface including a third temperature sensor integrated therein.
13. A photo-thermal targeted treatment system for targeting a chromophore embedded in a medium, the system including a controller; a photo-thermal treatment unit; and a temperature measurement system for measuring a temperature of a measured surface covering at least a portion of the medium. The controller is configured for administering a treatment protocol using the photo-thermal treatment unit. The temperature measurement system includes 1) a first temperature sensor, and 2) a reference surface with a second temperature sensor integrated therein, wherein the first temperature sensor includes a field of view covering both at least a portion of the measured surface and at least a portion of the reference surface.
14. The photo-thermal targeted treatment system of Item 13, wherein a first measurement taken by the first temperature sensor is compared to a second measurement taken by the second temperature sensor for use in calibrating the first temperature measurement with respect to the second temperature measurement.
15. The photo-thermal targeted treatment system of Item 14, wherein the first and second measurements are taken in situ during the treatment protocol.
16. The photo-thermal targeted treatment system of Item 15, wherein the first and second measurements are used by the controller to modify the treatment protocol in progress.
17. The photo-thermal targeted treatment system of Item 16, wherein the first and second measurements are used by the controller to modify an initialization timing of the treatment protocol in accordance therewith.
18. The photo-thermal targeted treatment system of Item 16, wherein the first and second measurements are used by the controller to terminate the treatment protocol in accordance therewith.
19. The photo-thermal targeted treatment system of Item 13, wherein the reference surface includes a texture thereon.
20. The photo-thermal targeted treatment system of Item 19, wherein the texture is configured for directing radiation, other than from the reference surface, away from the field of view of the first temperature sensor.
21. The photo-thermal targeted treatment system of Item 20, wherein the texture includes a sawtooth pattern.
22. The photo-thermal targeted treatment system of Item 13, wherein the temperature measurement system is integrated into the photo-thermal treatment unit.
23. The photo-thermal targeted treatment system of Item 13, wherein a time response of the measured surface temperature (i.e., epidermis temperature) is used to estimate the underlying dermis temperature, thereby providing a more accurate estimate of temperature of the sebaceous gland targeted by the photo-thermal targeted treatment system.

24. A method for continuously calibrating a temperature measurement system for use with a dermatological treatment, the method including: 1) using a first temperature sensor, simultaneously taking a first measurement of a measured surface and a first reference measurement of a reference surface; 2) using a second temperature sensor embedded within a reference surface, taking a second reference measurement of the reference surface; 3) calculating a comparison value between the first and second reference measurements; and 4) calibrating the first temperature sensor in accordance with the comparison value.

Figure 8:
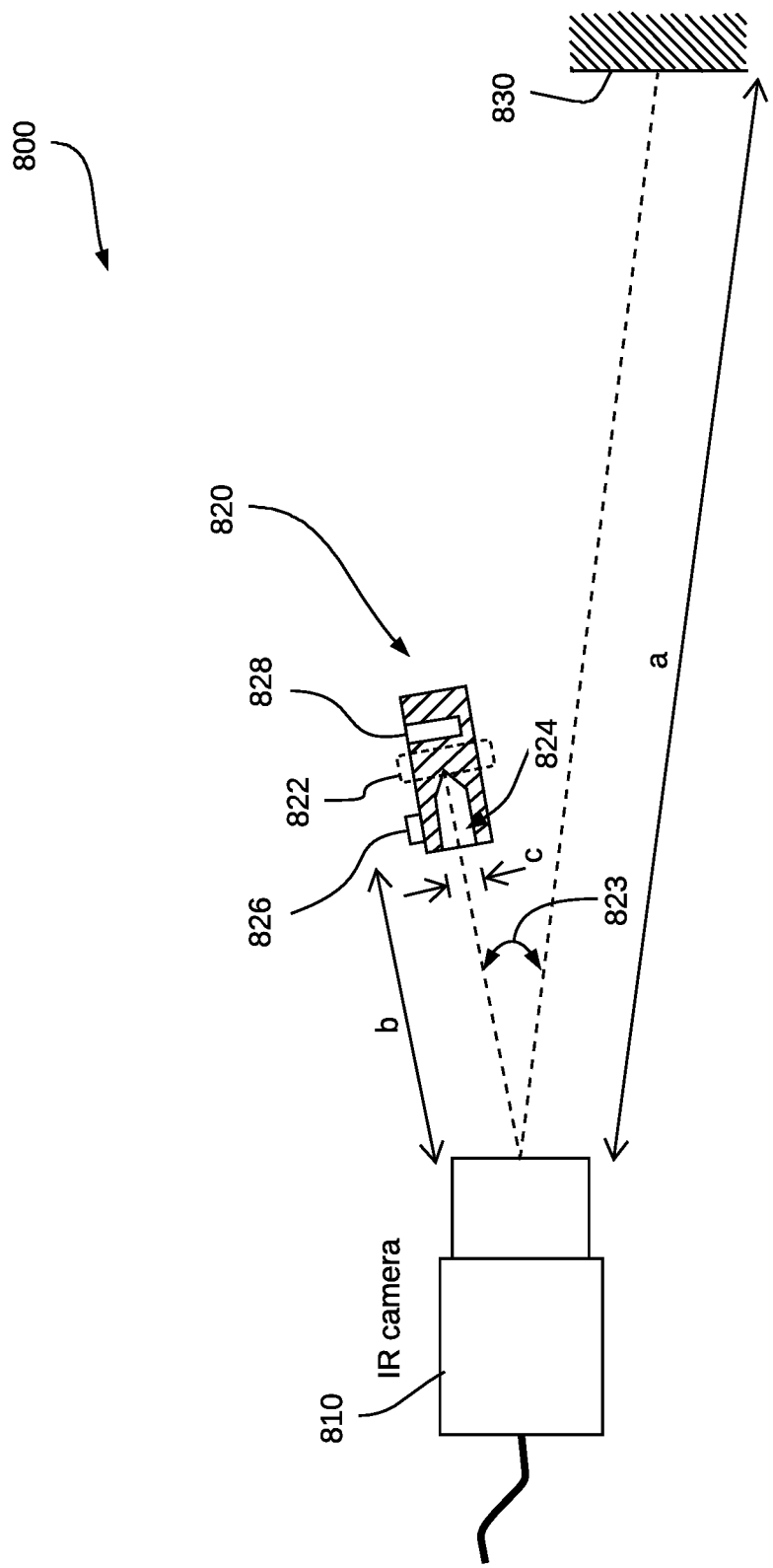
FIG. 8 is a simplified diagram of a calibration arrangement for use with a scanner apparatus, in accordance with an embodiment.

FIG. 8 is a simplified diagram of a calibration arrangement for use with a scanner apparatus, in accordance with an embodiment. In particular, FIG. 8 shows core components of a calibration arrangement 800 suitable for incorporation into a scanner (not shown). In certain embodiments, calibration arrangement 800 may include an IR camera 810 and a reference assembly 820. Reference assembly 820 may include a reference surface 822 within a FoV 823 of IR camera 810. In embodiments, the reference surface is characterized by a reference emissivity value approximately equal to a measured emissivity value of the measured surface.

In the example shown in FIG. 8, reference surface 822 (generally indicated by a region enclosed by dashed lines, located within an opening 824 such that IR camera 810 may obtain a temperature reading of reference surface 822 through opening 824. Taking the temperature reading of reference surface 822 located within opening 824 may be advantageous, for example, in the presence of a cooling air stream and/or laser energy near reference assembly 820, as is the case in a scanner arrangement illustrated in FIGS. 1 and 2. With reference surface 822 being within FoV 823 of IR camera 810 while protected from the cooling air stream and/or laser energy, the temperature of reference surface 822 may be more stable than if the reference surface were exposed to the cooling air stream and/or laser energy within the scanner apparatus.

Reference assembly 820 further includes a temperature sensor 826 for measuring the temperature of reference surface 822. Temperature sensor 826 may include, for example, a contact sensor such as that used in conjunction with reference surface 300 discussed above. Temperature sensor 826 may be configured to provide an independent reading of reference surface 822, to which the temperature reading obtained using IR camera 820 may be compared.

Additionally, reference assembly 820 may further include a heater 828. In embodiments, heater 828 is configured for heating reference surface 822 to a temperature similar to that of a skin surface 830 in the treatment area, at which the photo-thermal targeted treatment is being administered. It is recognized herein that ensuring the temperature at reference surface 822 is similar to that of skin surface 830, such that the temperature measured by IR camera 810 at skin surface 830 is similar to that measured at reference surface 822, aids in improving the accuracy of the subsequent calibration process, as described herein. For example, the heater may be configured to heat the reference surface to an elevated temperature within 0-20° C. or less of skin surface 830 according to, for instance, an initial measurement of skin surface 830 using IR camera 810. Additionally, in embodiments heater 828 may be replaced by a thermo-electric cooler (TEC) or one or more combinations of heating and cooling devices to enable adjustment of the reference surface temperature over a wide range, such as 40-55° C. corresponding to the expected skin surface temperature as measured during the application of the photo-thermal treatment protocol.

Figure 9:
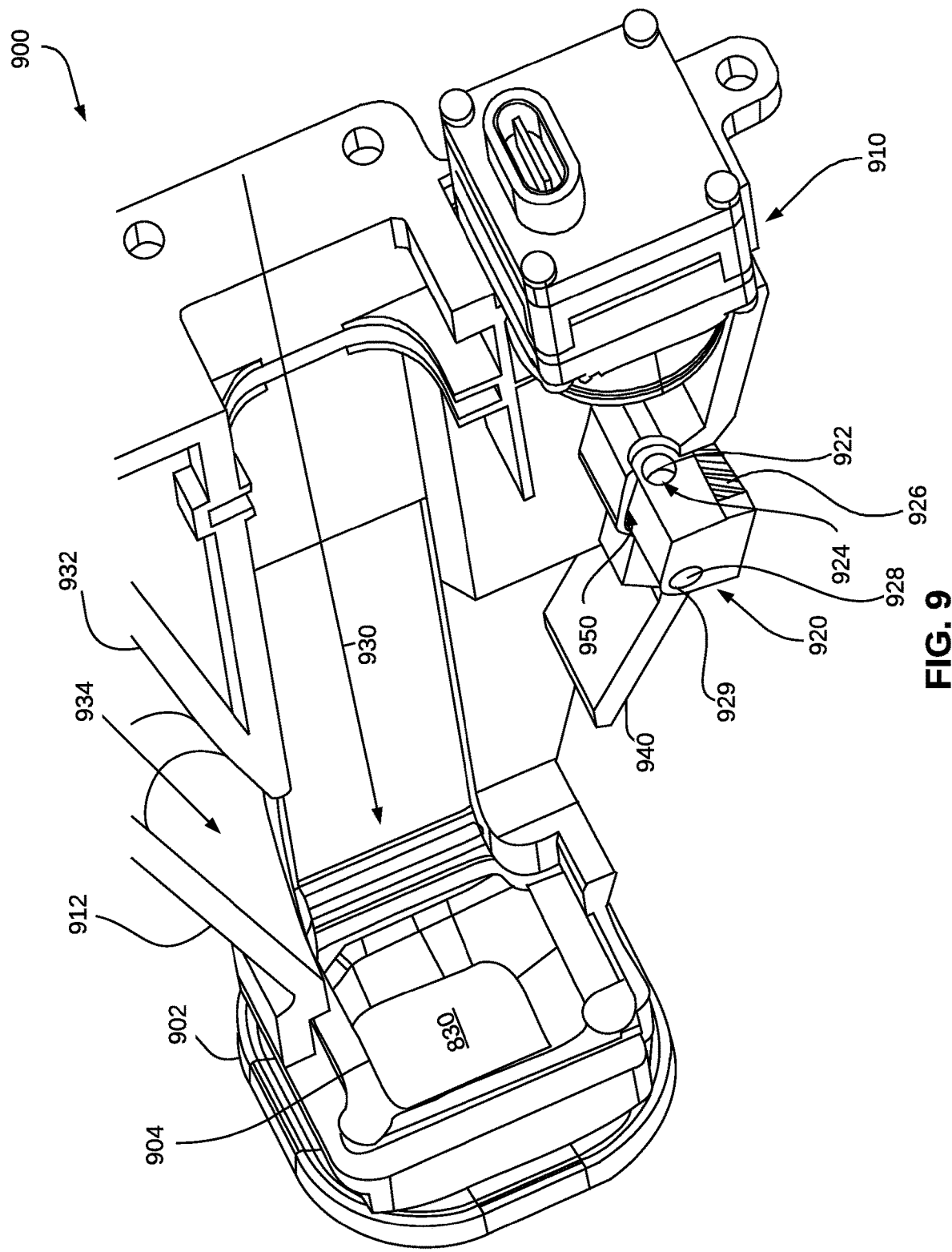
FIG. 9 shows a partial cut-away view of the scanner arrangement of FIG. 1, in certain embodiments.

FIG. 9 shows a partial cut-away view of the scanner arrangement of FIG. 9, in certain embodiments. As shown in FIG. 9, a portion of a scanner arrangement 900 includes a treatment tip 902 in contact with skin surface 830 at a treatment area. Treatment tip 902 includes a treatment aperture 904, through which a portion of skin surface 830 is visible within the FoV of an IR camera 910. An outer enclosure 912 of scanner arrangement 900 (only partially shown in FIG. 9) supports IR camera 910 relative to a reference assembly 920, in an embodiment. Reference assembly 920 includes a reference surface 922 within an opening 924, with a temperature sensor 926 for measuring the temperature of reference surface 922. In embodiments, reference assembly further includes a heater 928, inserted into a heater hole 929, for providing controlled heating of reference surface 922. Operation of heater 928 may be controlled by a control signal from the same controller that controls the operation of the air cooling and laser as well as receiving the temperature readings from IR camera 910 and temperature sensor 926. In embodiments, the heater may be controlled via closed-loop feedback from contact, temperature sensor 926 to maintain reference surface 922 at a target temperature.

In certain embodiments of operating the scanner arrangement of FIG. 9, a self-calibration routine may be performed for IR camera 910 by setting reference surface 922 at a first target temperature. Optionally, the self-calibration routine may be repeated with reference surface 922 at a second target temperature, different from the first target temperature. Further, the self-calibration routine may be repeated at additional different temperatures of the reference surface so as to calibrate the IR camera readings to the slope of the temperature drift as well as drift in the sensor gain. That is, by performing the calibration at two or more different temperatures, the calibration process may take into account both measurement offset (i.e., reference surface temperature measured by IR camera 810 adjusted by the reference surface temperature) and gain (i.e., the slope of the measured temperature versus actual target temperature over a range of target temperatures). As an example, the reference temperature may be set at 5° C., representing a low end of potentially measured skin temperature during a pre-cooling phase prior to the initiation of the treatment protocol. Then, the reference temperature may be set at a higher temperature, such as 45° C., at which the treatment is effective.

For instance, the first target temperature may be set at a minimum expected temperature from the measured skin surface at the treatment area, and the second target temperature may be set at a maximum expected temperature from the measured skin surface during treatment. In this way the calibration process may be particularly defined for accuracy in the expected operational temperature range of the photo-thermal energy treatment system.

In embodiments, scanner arrangement 900 is connected with a laser (not shown) for providing laser energy along a laser beam path 930 toward skin surface 830. Further air cooling of skin surface 830 may be provided through a cooling air duct 932 along a cooling air path 934. As described above, having reference surface 922 enclosed within an opening inside reference assembly 920 assists in ensuring the temperature reading at reference surface 922 is not affected by the cooling air or laser energy provided at skin surface 830. Optionally, a baffle or fin 940 may be provided as a part of scanner arrangement 900 to further deflect any stray cooling air and/or laser energy from impinging on IR camera 910 and/or reference assembly 920.

In particular, reference surface 922 is positioned such that the portion of the reference surface within the FoV of IR camera 910 is isolated from any stray cooling air flow and/or stray laser energy. Further, the temperature of the reference surface may be controlled with heater 928. Having reference surface 922 at a temperature near the measured temperature of the treatment area also serves to improve the accuracy of the calibration process, which may include, for example, offsetting (e.g., adjusting the measurements taken by the IR camera in accordance with the reference surface temperature) and accounting for gain (e.g., using the slope of the measured temperature versus actual target temperature over a range of target temperatures in adjusting for non-uniformity in the IR camera gain at different temperatures), to name a few non-limiting examples.

In certain embodiments, outer enclosure 912 may include a cut-out or molded opening 950 for accommodating reference assembly 920 therein. Cut-out 950 may further protect reference assembly from being affected by cooling air and laser energy conditions inside of scanner arrangement 900 such that the temperature reading at reference surface 922 is relatively more stable compared to the temperatures within scanner arrangement 900 and/or at skin surface 830. Further, with reference assembly 920 being insertable outside of scanner arrangement 900, any malfunctions with reference assembly 920 may be readily addressed, and reference assembly 920 may be easily connected and addressed by control electronics independently from the rest of the components of scanner arrangement 900.

Figure 10:
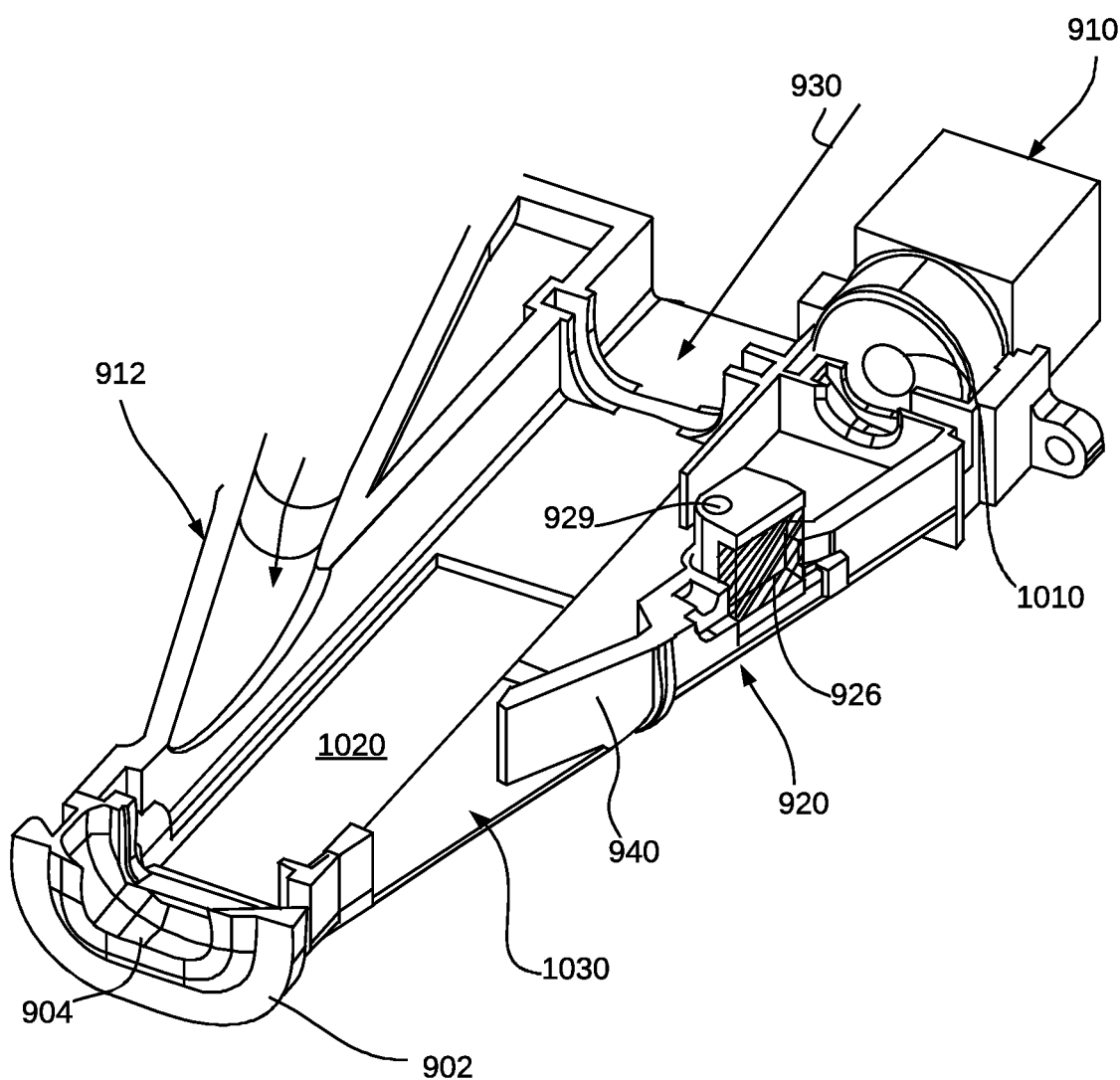
FIG. 10 shows another partial cut-away view of a reference block and an IR camera assembly for use with the scanner arrangement of FIG. 9, in certain embodiments.

FIG. 10 shows another partial cut-away view of a reference block and an IR camera assembly for use with the scanner arrangement of FIG. 9, in certain embodiments. As visible in FIG. 10, IR camera 910 includes a camera aperture 1010, through which both the skin surface of the treatment area (not shown in FIG. 10) and reference surface 922 (not visible in FIG. 10) of reference assembly 920 are within the FoV of IR camera 910. Optionally, a clear windows 1020 may be provided at one or more sides or scanner arrangement 900 for the user of the photo-thermal targeted treatment system to visually confirm proper placement of treatment tip 902 and treatment window 904 at the desired treatment area of the patient. In embodiments, an area between fin 940 and treatment tip 902 may include a vent opening 1030 for venting excess cooling air flow out of scanner arrangement 900. In embodiments, the shape and location of vent opening 1030 may be configured to cooperate with fin 940 to assist in directing vented excess cooling air flow away from reference assembly 920.

Figure 11:
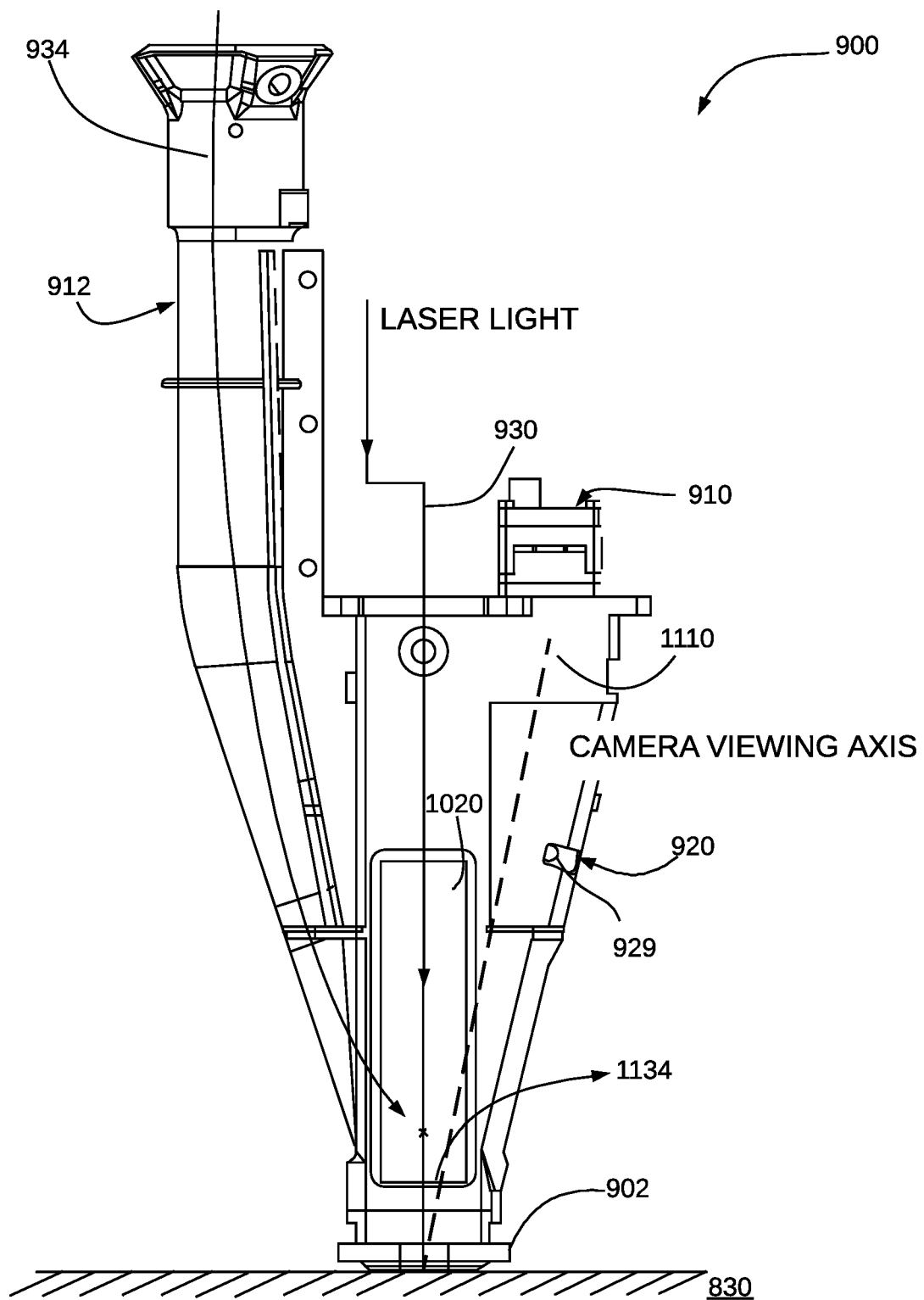
FIG. 11 shows a side view of the scanner arrangement of FIG. 9, in certain embodiments.

FIG. 11 shows a side view of the scanner arrangement of FIG. 9, in certain embodiments. As shown in FIG. 11, the path of laser energy (represented by arrow 930) and cooling air path 934 toward skin surface as well as excess cooling air flow path (represented by an arrow 1134) are superimposed on scanner arrangement 900. Further, a camera viewing axis, as represented by a dashed line 1110, shows a line along which IR camera 910 may be aimed for including both skin surface 830 and reference assembly 920 (only partially visible in FIG. 11) in its field of view.

Figure 12:
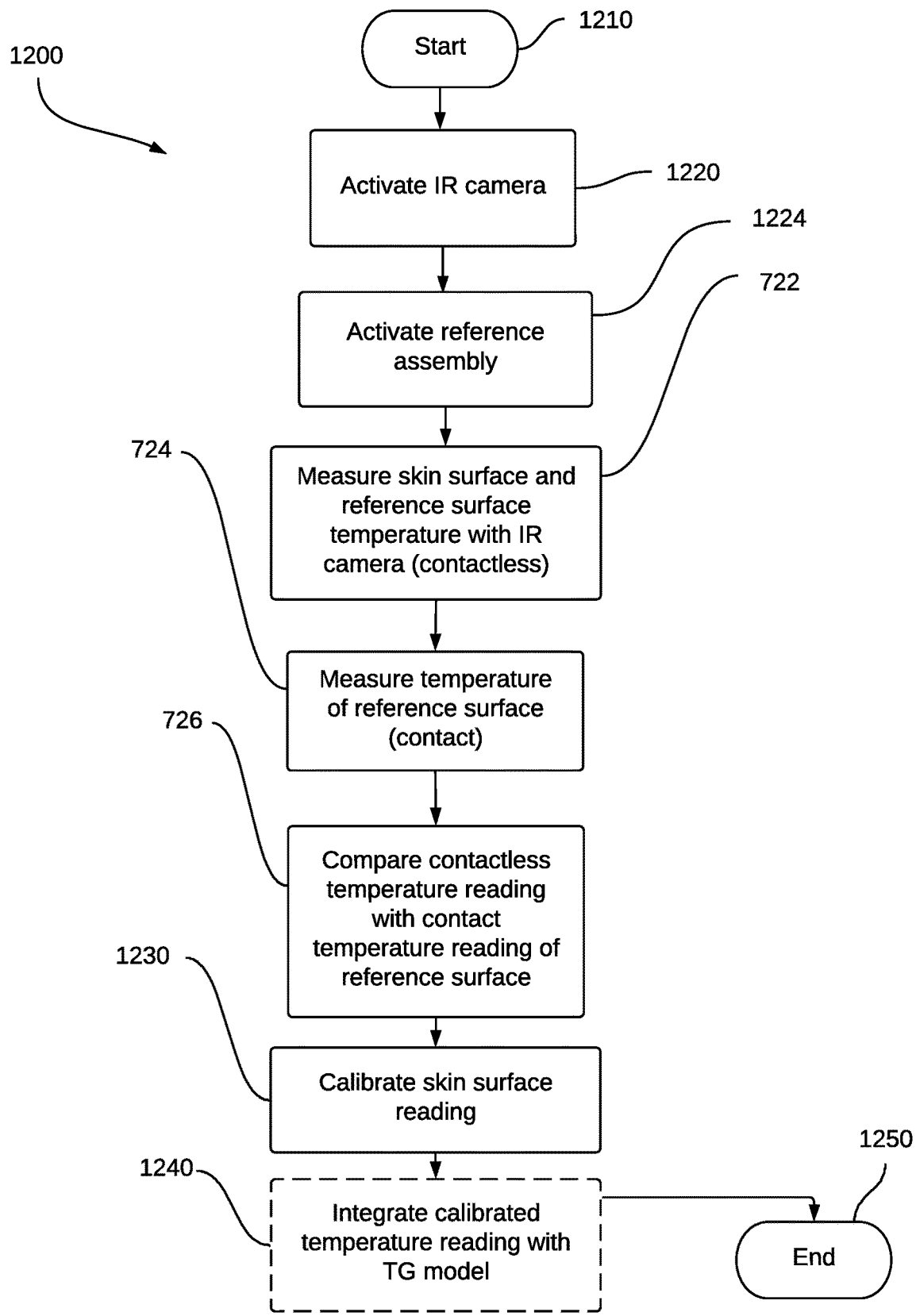
FIG. 12 shows a flow chart illustrating a process for calibrating a scanner arrangement for use in a photo-thermal targeted treatment system, in accordance with an embodiment.

FIG. 12 shows a flow chart illustrating a process for calibrating a scanner arrangement for use in a photo-thermal targeted treatment system, in accordance with an embodiment. As shown in FIG. 12, a process 1200 begins with a start step 1210, then proceeds to a step 1220 to activate the IR camera, such as IR camera 910 described above, and a step 1224 to activate a reference assembly, such as reference assembly 920 described above. Like previously discussed process 700 of FIG. 7, process 1200 proceeds to step 722 to measure the skin surface and reference surface temperatures with the IR camera in a contactless manner, step 724 to measure the temperature of the reference surface in a contact measurement, then the contactless and contact temperature readings are compared in step 726.

Then, in a step 1230, the comparison of step 726 is used to self-calibrate the temperature reading at the skin surface. For example, step 1230 may include offsetting and gain adjustment, as briefly described above with respect to FIG. 9. A variety of calibration methods may be contemplated, given the additional and controlled temperature measurements provided by the integration of the reference assembly described herein.

Optionally, the self-calibrated temperature measurement at the skin surface may be integrated with a thermal gradient model to calculate and monitor a thermal gradient profile established below the skin surface at the treatment area in a step 1240. In particular, given the frequency of data capture (e.g., 30 Hz and greater) and sufficient data processing speed, changes in the thermal gradient profile at depths below the skin surface may be monitored essentially in real time before, during, and after the laser energy application, thus aiding in enhancing safety and patient comfort during the photo-thermal treatment process.

Figure 13:
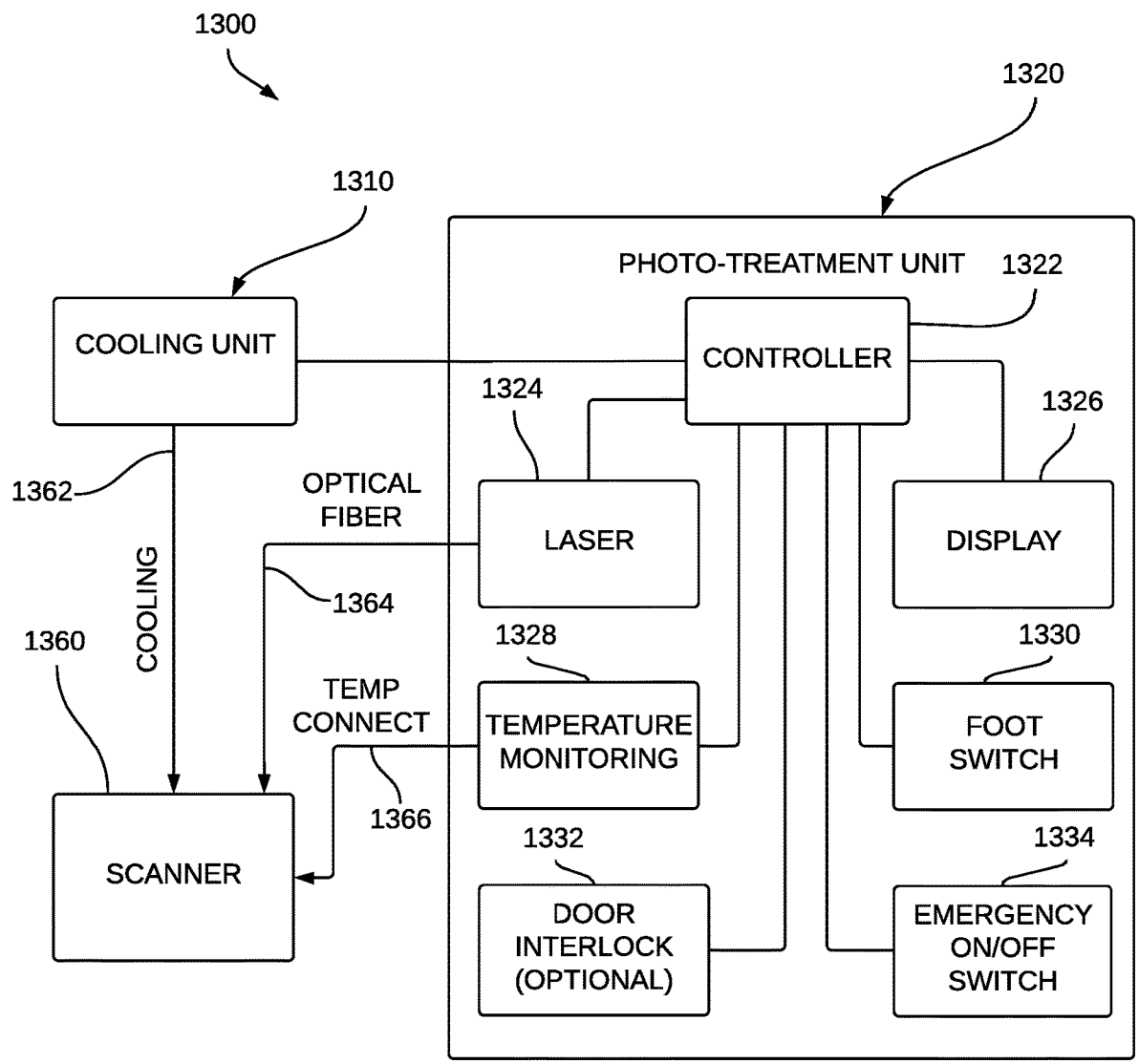
FIG. 13 illustrates an exemplary photothermal targeted treatment system, in accordance with an embodiment.

FIG. 13 shows an exemplary photo-thermal targeted treatment system for targeting a target, wherein the target includes specific chromophores embedded in a medium, and heating the target to a sufficiently high temperature so as to damage the target without damaging the surrounding medium. The system can be used, for example, for photo-thermal ablation of sebaceous glands in a targeted fashion, where sebum is the chromophore embedded within the sebaceous gland, while sparing the epidermis and dermis surrounding the target sebaceous glands.

Still referring to FIG. 13, a photo-thermal targeted treatment system 1300 includes a cooling unit 1310 and a photo-treatment unit 1320. Cooling unit 1310 provides a cooling mechanism for a cooling effect, such as by contact or by direct air cooling, to treatment area, namely the outer skin layer area overlying the target sebaceous gland. Cooling unit 1310 is connected with a controller 1322 within photo-treatment unit 1320. It is noted that, while controller 1322 is shown to be contained within photo-treatment unit 1320 in FIG. 13, it is possible for the controller to be located outside of both cooling unit 1310 and photo treatment unit 1322, or even within cooling unit 1310.

Controller 1322 further controls other components within photo-treatment unit 1320, such as a laser 1324, a display 1326, a temperature monitoring unit, a foot switch 1330, a door interlock 1332, and an emergency on/off switch 1334. Laser 1324 provides the laser power for the photo-treatment protocol, and controller 1322 regulates the specific settings for the laser, such as the output power and pulse time settings. Laser 1324 can be a single laser or a combination of two or more lasers. If there more than one laser is used, the laser outputs are combined optically to function as one more powerful laser. Alternatively, multiple lasers may be incorporated into a multi-treatment device enabling the application of different treatments using different wavelengths. Similarly, different wavelengths with different skin penetration depths may be strategically utilized to establish a desired thermal gradient (i.e., different temperatures at different depths at the treatment site). Display 1326 can include information such as the operating conditions of cooling unit 1310, laser 1324, and other system status.

Temperature monitoring unit 1328 is used to monitor the temperature of the skin surface in the treatment area, for example, and the measured skin surface temperature at the treatment area is used by controller 1322 to adjust the photo-treatment protocol. For instance, temperature monitoring unit 1328 may receive temperature information from a self-calibrated temperature sensing apparatus as described above. Controller 1322 also interfaces with footswitch 1330 for remotely turning on or off laser 1324 and/or cooling unit 1310. Additionally, door interlock 1332 can be used as an additional safety measure such that, when the door to the treatment room is ajar, door interlock 1332 detects the condition and instructs controller 1322 to not allow photo-treatment unit 1320, or at least laser 1324, to operate. Furthermore, emergency on/off switch 1334 can be provided to quickly shut down photo-thermal targeted treatment system 1300 in case of an emergency. In another modification, additional photodiodes or other sensors can be added to monitor the power level of the energy emitted from laser 1324.

Continuing to refer to FIG. 13, photo-thermal targeted treatment system 1300 further includes a scanner 1360, which is the portion of the device handheld by the user in applying the treatment protocol to the subject. Scanner can be formed, for example, in a gun-like or stick-like shape for ease of handling by the user, such as illustrated in FIGS. 9-11 described above. Scanner 1360 is connected with cooling unit 1310 via a cooling connection 1362, such that the cooling protocol can be applied using scanner 1360. Additionally, the output from laser 1324 is connected with scanner 1360 via an optical fiber delivery 1364, such that the photo-treatment protocol can be applied using scanner 1360. Scanner 1360 is connected via a temperature connection 1366 to temperature monitoring unit 1328, so as to feedback the skin temperature at the treatment area, for example, to controller 1322.

Figure 14:
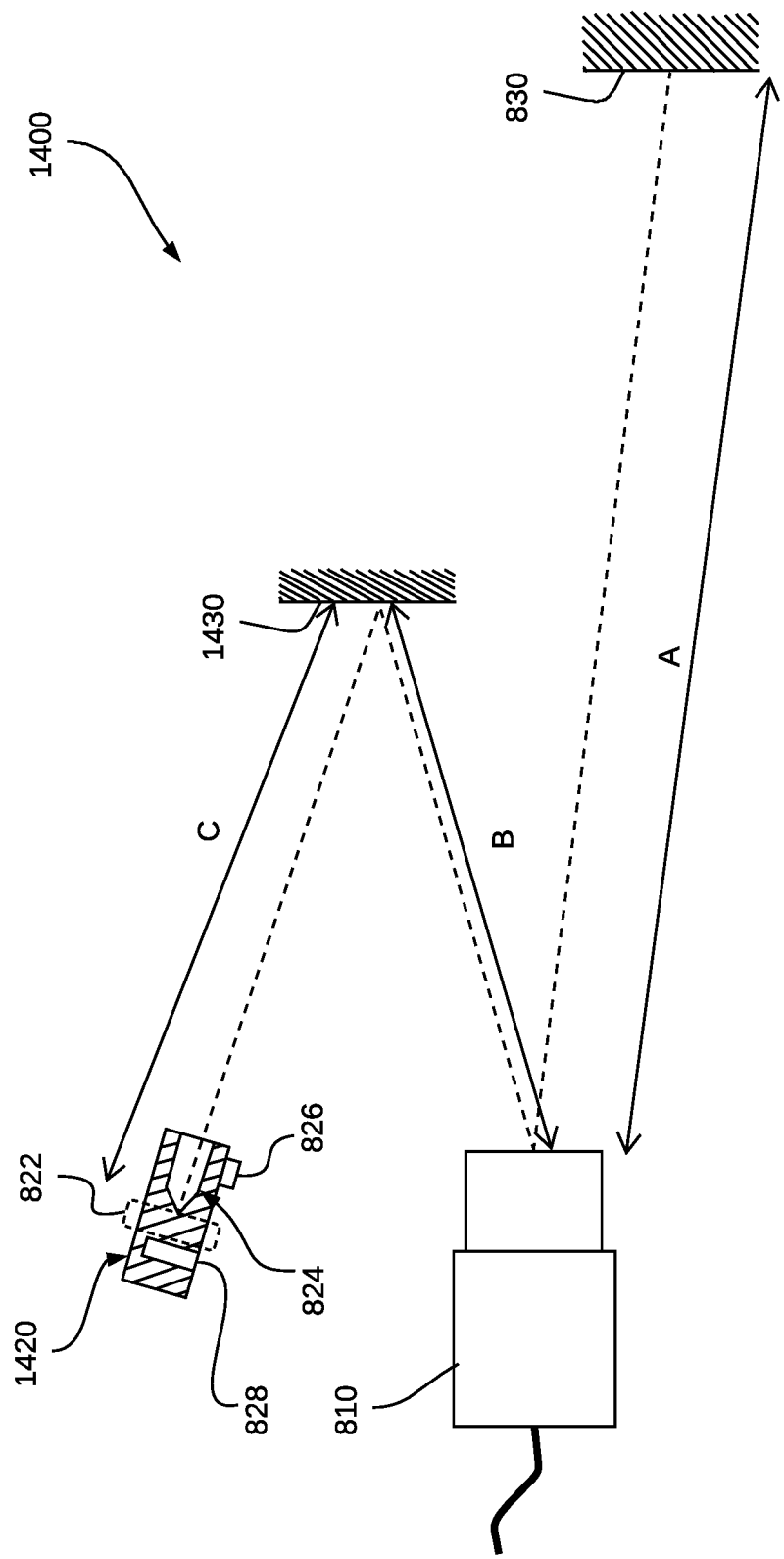
FIG. 14 illustrates a simplified diagram of another calibration arrangement for use with a scanner apparatus, in accordance with an embodiment.

FIG. 14 illustrates a simplified diagram of another calibration arrangement for use with a scanner apparatus, in accordance with an embodiment. In particular, FIG. 14 shows core components of a calibration arrangement 1400 suitable for incorporation into a scanner, similar to calibration arrangement 800 of FIG. 8 described above. In embodiments, calibration arrangement 1400 may include a reference assembly 1420, which includes components similar to those of reference assembly 820, except oriented in a similar direction as IR camera 810, such that IR camera "sees" reference assembly 1420 via an IR mirror 1430. By ensuring path length A between IR camera 810 and skin surface 830 is similar in length to the sum of path length B between IR camera 810 and IR mirror 1430 with path length C between IR mirror 1430 and reference surface 822 within reference assembly 1420, both reference surface 822 and skin surface 830 are in focus at IR camera 810.

The positioning of reference assembly 1420 may be particularly advantageous in that reference assembly 1420 may be positioned adjacent to IR camera 810. In this way, reference assembly 1420 may be exposed to stray cooling and heating energies experienced by IR camera 810, and any adjustments required of heater 828 to keep reference surface 822 at a desired temperature may be taken into consideration in the calibration protocol of IR camera 810.

Figure 15:
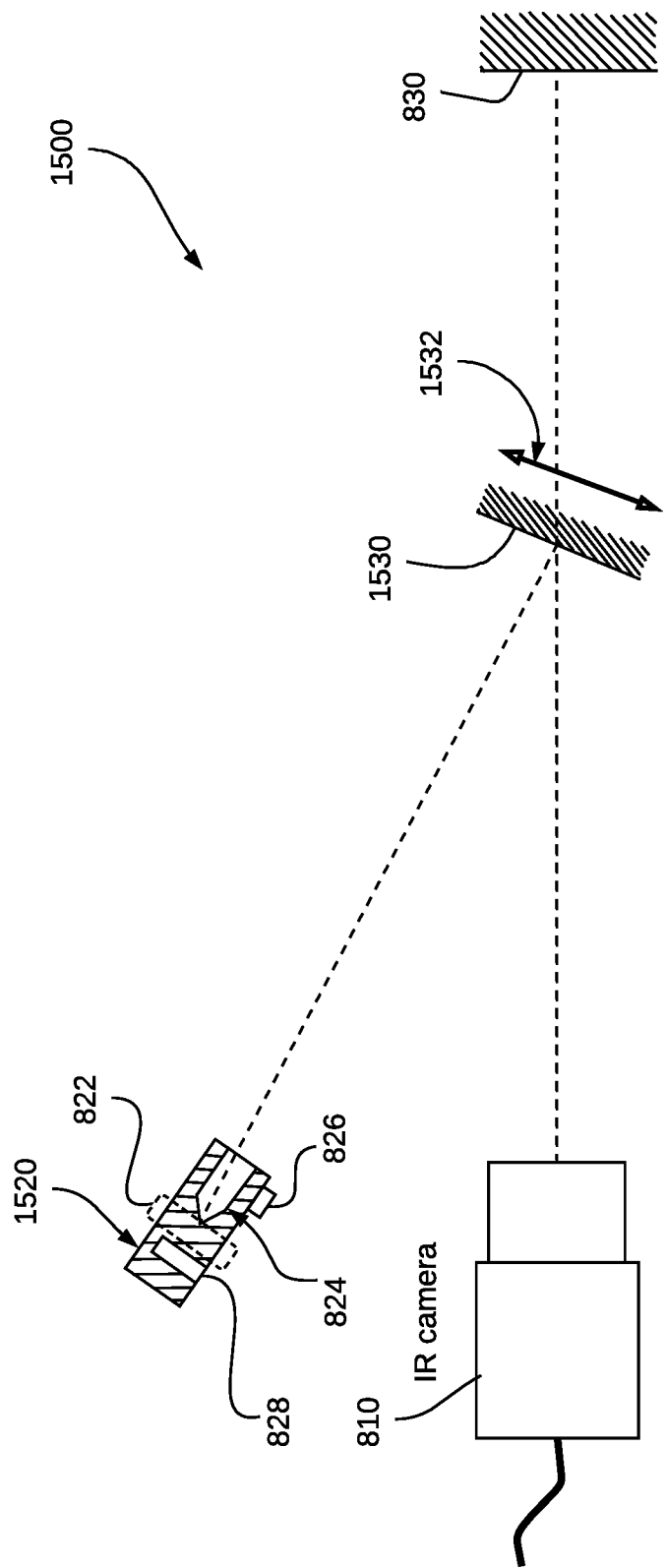
FIG. 15 illustrates a simplified diagram of another calibration arrangement for use with a scanner apparatus, in accordance with an embodiment.

FIG. 15 illustrates a simplified diagram of another calibration arrangement for use with a scanner apparatus, in accordance with an embodiment. As shown in FIG. 14, a calibration arrangement 1500 includes a similar positioning of a reference assembly 1520 with respect to IR camera 810. In embodiments, calibration arrangement 1500 includes a movable IR mirror 1530, which may be moved in and out of the IR camera FoV (as indicated by a double-headed arrow 1532) to enable rapid calibration correction. In particular, with the positioning of the components shown in FIG. 15, reference surface 822 and skin surface 830 may be imaged on the same area of the focal plane array of IR camera 810 such that any spatial non-uniformity in the focal plane sensitivity may be accounted for in the calibration process.

Figure 16:
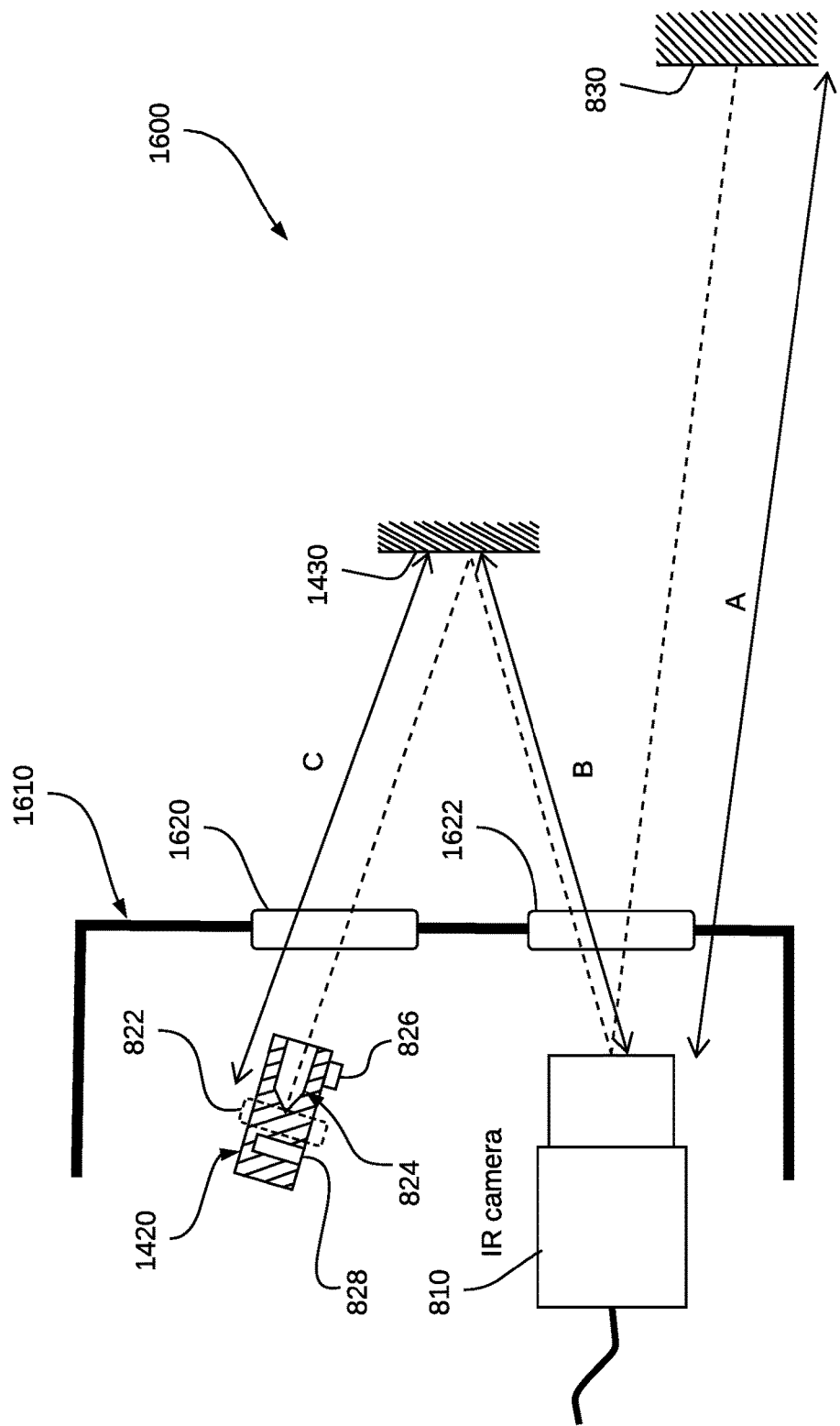
FIG. 16 illustrates a simplified diagram of another calibration arrangement for use with a scanner apparatus, in accordance with an embodiment.

FIG. 16 illustrates a simplified diagram of another calibration arrangement for use with a scanner apparatus, in accordance with an embodiment. As shown in FIG. 16, a calibration arrangement 1600 includes a similar set of components as calibration arrangement 1400 of FIG. 14. Additionally, calibration arrangement 1600 includes an enclosure 1610 configured for thermally isolating IR camera 810 and reference assembly 1420 from temperature fluctuations that may be present within the overall scanner arrangement, while enabling the transmission of infrared light therethrough. For example, enclosure 1610 may be formed of a plastic, an acrylic, layers of materials with an air or vacuum gap, or other materials suitable for providing thermal isolation of the IR camera and the reference assembly. Enclosure 1610 may include first and second openings 1620 and 1622, each of which may include an IR window for transmitting infrared light therethrough while preventing wavelengths outside of the IR range from entering enclosure 1610. In certain embodiments, the IR window disposed at first and/or second openings 1620 and 1622 may include a selective wavelength coating for selectively transmitting specific desired wavelengths (e.g., a range of IR wavelengths at which the IR camera is sensitive) therethrough. The coating may also selectively block the laser wavelength to prevent stray light from entering IR camera 810. In embodiments, enclosure 1610 may be integrally formed from the scanner arrangement.

Figure 17:
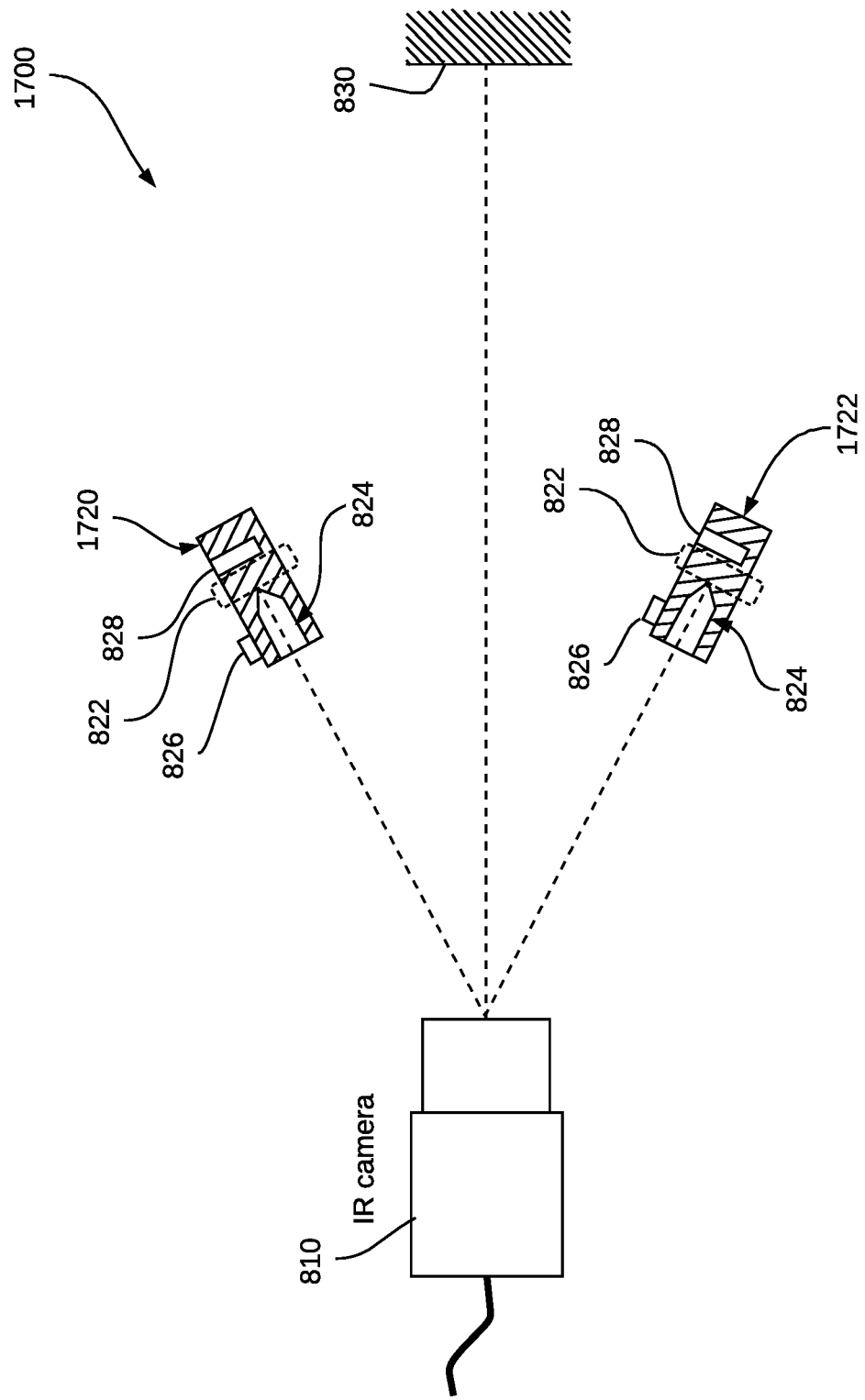
FIG. 17 illustrates a simplified diagram of another calibration arrangement for use with a scanner apparatus, in accordance with an embodiment.

FIG. 17 illustrates a simplified diagram of another calibration arrangement for use with a scanner apparatus, in accordance with an embodiment. As shown in FIG. 17, a calibration arrangement 1700 includes first and second reference assemblies 1720 and 1722. In embodiments, the respective reference surfaces of first and second reference assemblies 1720 and 1722 may be set at different temperatures to enable simultaneous calibration of IR camera 810 to different temperatures, without having to adjust the temperature of a single reference surface to accommodate serial calibration over multiple temperatures. Again, with the availability of reference assemblies set at two different temperatures, the calibration process may take into account both temperature drift and non-uniformity in gain by the IR camera at different temperatures. As described above, the first and second reference assemblies may be set, for example, at minimum and maximum anticipated measured temperature at skin surface 830 (e.g., at 5° C. and 45° C.) to tailor the calibration process to the temperature range of interest in the treatment protocol.

Figure 18:
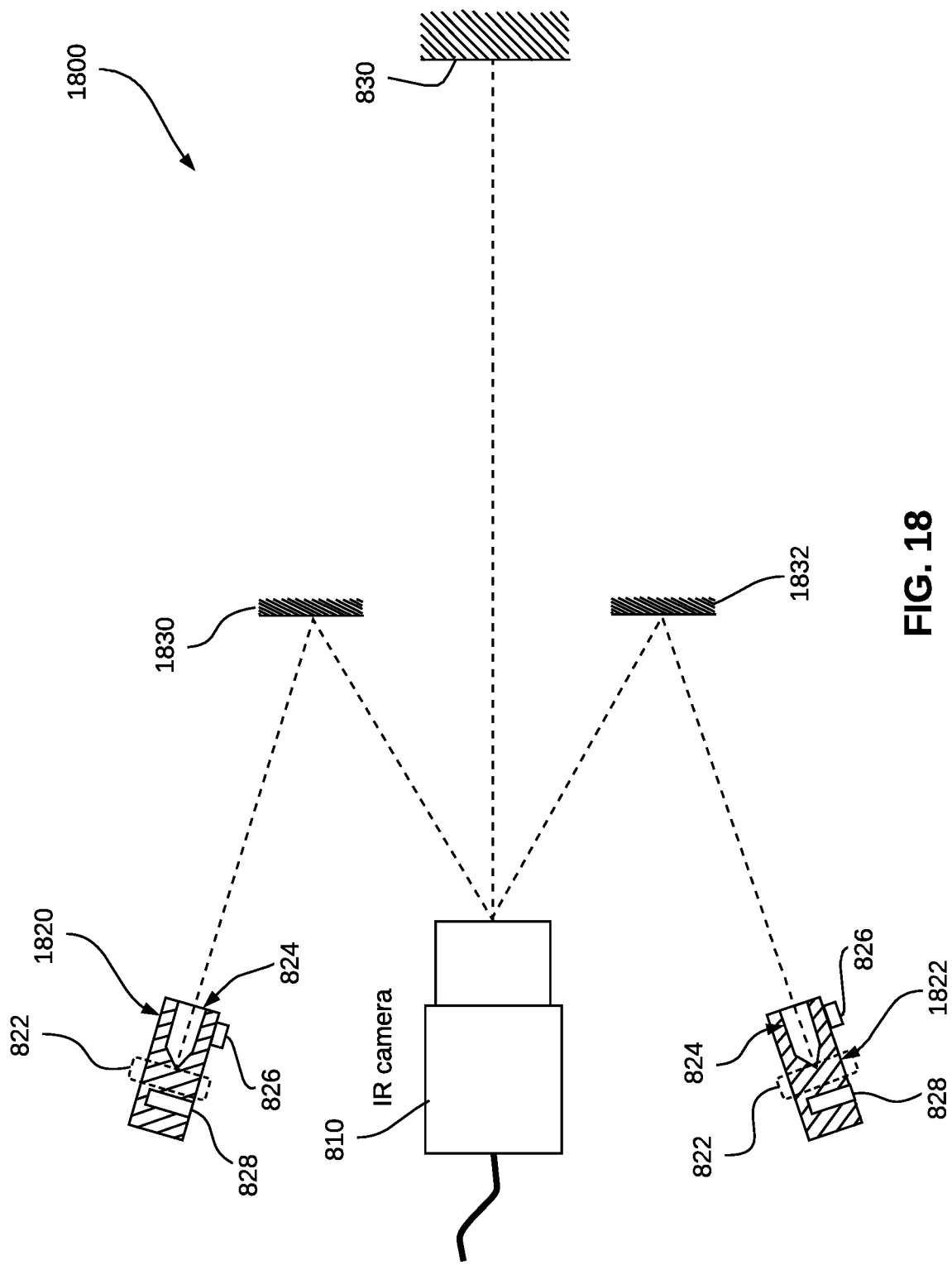
FIG. 18 illustrates a simplified diagram of another calibration arrangement for use with a scanner apparatus, in accordance with an embodiment.

FIG. 18 illustrates a simplified diagram of another calibration arrangement for use with a scanner apparatus, in accordance with an embodiment. A calibration arrangement 1800 includes first and second reference assemblies 1820 and 1822, respectively optically coupled with first and second IR mirrors 1830 and 1832. That is, calibration arrangement 1800 combines the advantages of the positioning of the reference surfaces with respect to the IR camera to simultaneously bring the reference surfaces and skin surface 830 into focus at the IR camera, while enabling the dual reference surface calibration as described above with respect to FIG. 17.

Other modifications of the reference assembly are anticipated and are considered part of the present disclosure. For example, the reference surface may be provided with a coating or a texture to provide uniform emissivity across the reference surface, thus promoting a Lambertian behavior of the reference surface emission. Suitable coatings may be, for example, anodized aluminum or another anodic oxide with known, well-characterized emissivity characteristics. Additional thin film coatings may be applied at the reference surface to, for example, emission or blocking of emission at specific wavelengths or wavelength bands.

Additionally, the various reference assemblies described above may be formed, 3D printed, injection molded, or otherwise integrally formed as a part of the scanner assembly itself. For example, the reference assembly may be inserted into a pre-formed cavity formed in the outside portion the scanner, as shown in FIGS. 9 and 10, or in an internal compartment within the scanner. In other embodiments, the reference assembly and IR camera may be separately assembled then retrofitted to the internal cavity or an external portion of any device for which accurate temperature measurement and calibration may be required. For example, a separately assembled reference assembly may be attached to an existing temperature measurement system for providing a more accurate calibration of the system in operation.

There may be particular advantages in installing the reference assembly within the internal cavity of the scanner to be able to take into account any thermal back reflections from the skin surface under treatment, which may otherwise not be detectable outside of the scanner. While such back reflections from the skin surface being treated may be relatively small compared to the thermal gradient being established below the skin surface, the back reflections are known to provide a measurable difference in the temperature detection behavior at the IR camera during clinical use. Thus, by taking into account such back reflections in the calibration protocol of the IR camera, the accuracy of the temperature measurement by the IR camera may be further improved.

In operation, the calibration process using the reference assembly may be performed periodically during the lifetime of the photo-thermal targeted treatment system, ahead of each treatment application, or even in real time during the application of the treatment protocol. The controller for the photo-thermal targeted treatment system may be also used to operate the calibration apparatus to ensure accurate temperature measurements even during the application of the photo-thermal treatment protocol.

In the specification, there have been disclosed embodiments of the invention and, although specific terms are employed, they are used in a generic and descriptive sense only and not for purposes of limitation. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

As used herein, the recitation of "at least one of A, B and C" is intended to mean "either A, B, C or any combination of A, B and C." The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The terms and expressions employed herein are used as terms and expressions of description and not of limitation, and there is no intention, in the use of such terms and expressions, of excluding any equivalents of the features shown and described or portions thereof. Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, by way of example only, the disclosure of a "protrusion" should be understood to encompass disclosure of the act of "protruding"—whether explicitly discussed or not—and, conversely, were there only disclosure of the act of "protruding", such a disclosure should be understood to encompass disclosure of a "protrusion". Such changes and alternative terms are to be understood to be explicitly included in the description.

The invention claimed is:

1. A photo-thermal targeted treatment system for targeting a chromophore embedded in a medium, the photo-thermal targeted treatment system comprising:
   a controller;
   a photo-thermal treatment unit; and
   a temperature measurement system for measuring a temperature of a measured surface covering at least a portion of the medium,
   wherein the controller is configured for administering a treatment protocol using the photo-thermal treatment unit,
   wherein the photo-thermal treatment unit is configured for providing a cooling air stream and laser energy toward the measured surface,
   wherein the temperature measurement system includes 1) a first temperature sensor and 2) a reference assembly,
   wherein the reference assembly includes an opening with a reference surface located within the opening, a second temperature sensor positioned in contact with the reference surface and configured for measuring temperature of the reference surface, and a heater for heating the reference surface in accordance with control signals from the controller, wherein the first temperature sensor is a contactless temperature sensor with a field of view covering at least a portion of the measured surface and at least a portion of the reference surface, and wherein the opening and the reference surface are configured to cooperate such that the reference surface is protected from direct exposure to the cooling air stream and the laser energy.

2. The system of claim 1, wherein a first measurement taken by the first temperature sensor is compared to a second measurement taken by the second temperature sensor for use in calibrating the first temperature measurement with respect to the second temperature measurement.

3. The system of claim 2, wherein the first and second measurements are taken in situ during the treatment protocol.

4. The system of claim 3, wherein the first and second measurements are used by the controller to modify the treatment protocol in progress.

5. The system of claim 4, wherein the first and second measurements are used by the controller to terminate the treatment protocol in accordance therewith.

6. The system of claim 1, wherein a time response of the measured surface temperature is used to estimate an underlying dermis temperature, thereby providing a more accurate estimate of the chromophore targeted by the photo-thermal targeted treatment system than would be possible without the temperature measurement system.

7. The system of claim 1, wherein the opening and the reference surface are configured to cooperate such that the reference surface is protected from direct exposure to the cooling air stream and the laser energy.

8. The system of claim 7, wherein the reference surface is set back from a mouth of the opening.

9. The system of claim 7, further comprising a baffle for directing stray portions of the cooling air stream and the laser energy away from the reference surface.

* * * * *